(12) United States Patent
Huber et al.

(10) Patent No.: US 6,630,499 B1
(45) Date of Patent: Oct. 7, 2003

(54) CONTROL OF ARTHROPODS IN ANIMALS

(75) Inventors: Scot Kevin Huber, Raleigh, NC (US); Yves Ribeill, Raleigh, NC (US); Susan Marie McComb, Bad Soden (DE); Michael James Malaska, Chapel Hill, NC (US); David Teh-Wei Chou, Raleigh, NC (US); Adalberto Perez de Leon, Wake Forest, NC (US)

(73) Assignee: Aventis CropScience, S.A., Lyons (FR)

( * ) Notice: Subject to any disclaimer, the term of this patent is extended or adjusted under 35 U.S.C. 154(b) by 0 days.

(21) Appl. No.: 10/342,203

(22) Filed: Jan. 15, 2003

Related U.S. Application Data

(60) Division of application No. 09/590,069, filed on Jun. 9, 2000, now Pat. No. 6,531,501, which is a continuation-in-part of application No. 09/457,869, filed on Dec. 10, 1999, now Pat. No. 6,160,002.

(60) Provisional application No. 60/111,857, filed on Dec. 11, 1998, and provisional application No. 60/140,680, filed on Jun. 24, 1999.

(51) Int. Cl.$^7$ .................... A61K 31/415; A61P 33/00
(52) U.S. Cl. .................... 514/407; 548/368.4
(58) Field of Search .................... 548/368.4; 514/407

(56) References Cited

U.S. PATENT DOCUMENTS

| | | |
|---|---|---|
| 4,863,937 A | 9/1989 | Gehring et al. |
| 4,931,461 A | 6/1990 | Jensen-Korte et al. |
| 5,232,940 A | 8/1993 | Hatton et al. |
| 5,556,873 A | 9/1996 | Huang et al. |
| 5,580,843 A | 12/1996 | Stetter et al. |
| 5,814,652 A | 9/1998 | Wu |
| 6,160,002 A | 12/2000 | Huber et al. |

FOREIGN PATENT DOCUMENTS

| | | |
|---|---|---|
| EP | 0296381 | 12/1988 |
| EP | 0301338 | 2/1989 |
| EP | 0511845 | 11/1992 |
| EP | 0659745 | 6/1995 |
| EP | 0811615 | 12/1997 |
| EP | 0846686 | 6/1998 |
| EP | 0295117 | 12/1998 |
| WO | 87/03781 | 7/1987 |
| WO | 93/06089 | 4/1993 |
| WO | 94/21606 | 9/1994 |
| WO | 97/07102 | 2/1997 |
| WO | 97/22593 | 6/1997 |
| WO | 98/24767 | 6/1998 |
| WO | 98/28277 | 7/1998 |
| WO | 98/28278 | 7/1998 |
| WO | 98/28279 | 7/1998 |
| WO | 98/40359 | 9/1998 |

OTHER PUBLICATIONS

Database WPI AN 1998–196351, XP–002136814, abstrace of JP 10 007509, published Jan. 13, 1998.

Huang, *Chemical Abstracts*, vol. 128, No. 111908 (abstract of JP 10 007509, Jan. 13, 1998), published by the American Chemical Society, Columbus, Ohio.

*Primary Examiner*—Robert W. Ramsuer
(74) *Attorney, Agent, or Firm*—Burns, Doane, Swecker & Mathis, L.L.P.

(57) ABSTRACT

A method of controlling parasites in or on an animal comprising orally administering to the animal a parasiticidally effective, substantially non-emetic 1-arylpyrazole.

57 Claims, No Drawings

CONTROL OF ARTHROPODS IN ANIMALS

CROSS-REFERENCE TO RELATED APPLICATIONS

This application is a divisional of U.S. patent application Ser. No. 09/590,069, filed Jun. 9, 2000, now U.S. Pat. No. 6,531,501, which is a continuation-in-part of U.S. patent application Ser. No. 09/457,869, filed Dec. 10, 1999, now U.S. Pat. No. 6,160,002, issued Dec. 12, 2000, which claims the priority of U.S. Provisional Application No. 60/111,857, filed Dec. 11, 1998, and of U.S. Provisional Application No. 60/140,680, filed Jun. 24, 1999, all of which are incorporated by reference in their entireties and relied upon.

BACKGROUND OF THE INVENTION

1. Field of the Invention

The present invention relates to a method of control of parasites in animals, compositions comprising a compound effective for said control and new compounds effective against parasites.

2. Related Art

The state of the art is represented by Hatton et al U.S. Pat. No. 5,232,940, Stetter et al U.S. Pat. No. 5,580,843, Huang et al U.S. Pat. No. 5,556,873, EP 0511845, WO 87/03781, WO 93/06089, WO 94/21606, WO 97/07102, WO 98/24767, WO 98/28277, WO 98/28278, WO 98/28279, EP 0295117, EP 0846686, EP 0659745, WO 97/22593 and EP 0811615.

It is generally a goal of agronomists and veterinarians to possess sufficient means to control pests, particularly arthropods, when they attempt to invade or attack mammals, particularly domestic animals and/or livestock. A classical method of controlling such pests has been the use of topical and/or systemic pesticides on or in the domestic animal which is being attacked. Generally effective treatments include the oral administration of insect growth regulators, such as lufenuron, or antihelminth compounds such as an ivermectin or an avermectin, or the topical application of the insecticide fipronil. It is advantageous to apply pesticides to animals in oral form so as to prevent the possible contamination of humans or the surrounding environment.

SUMMARY AND OBJECTS OF THE INVENTION

It is an object of the present invention to provide new pesticides which may be used in domestic animals.

Another object of the invention is to provide safer pesticides for domestic animals.

Another object of the invention is to provide new pesticides for domestic animals that are may be used in lower doses than existing pesticides.

These objects are met in whole or in part by the present invention.

The present invention provides a method of controlling parasites in or on an animal comprising administering orally to the animal a parasiticidally effective, substantially non-emetic amount of a 1-arylpyrazole of formula (I):

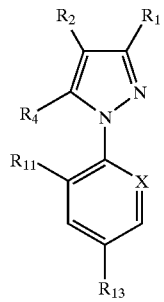

(I)

wherein:

$R_1$ is cyano, acetyl, $C(S)NH_2$, alkyl, haloalkyl, $C(=NOH)NH_2$ or $C(=NNH_2)NH_2$;

$R_2$ is $S(O)_nR_3$, $C_2$–$C_3$ alkenyl, $C_2$–$C_3$ haloalkenyl, cycloalkyl, halocycloalkyl or $C_2$–$C_3$ alkynyl;

$R_3$ is alkyl or haloalkyl;

$R_4$ is —N=C($R_5$)—Z—$R_6$, —N=C($R_5$)—N($R_7$)—$R_8$, or —N($R_9$)—C($R_5$)=$NR_6$;

$R_5$ is hydrogen, alkyl, or alkyl substituted by halogen, alkoxy, haloalkoxy or —S(O)$_m$$R_{15}$;

$R_6$ and $R_7$ each independently represent hydrogen, alkyl, $C_3$–$C_5$ alkenyl or $C_3$–$C_5$ alkynyl; or alkyl substituted by one or more halogen, alkoxy, haloalkoxy, amino, alkylamino, dialkylamino, cyano or —S(O)$_m$$R_{15}$; or alkyl substituted by phenyl or pyridyl each of which is optionally substituted with one or more groups selected from halogen, nitro and alkyl; or $R_6$ and $R_7$ may form together with the nitrogen to which they are attached a 3 to 7 membered ring which may additionally contain one or more heteroatoms selected from oxygen, nitrogen or sulfur;

$R_8$ is alkoxy, haloalkoxy, amino, alkylamino, dialkylamino, $R_{14}CO$— or —S(O)$_t$$R_{10}$;

$R_9$, $R_{10}$ and $R_{14}$ are alkyl or haloalkyl;

$R_{11}$ and $R_{12}$ are independently selected from halogen, hydrogen, CN and $NO_2$;

$R_{13}$ is selected from halogen, haloalkyl, haloalkoxy, —S(O)$_q$$CF_3$, and —$SF_5$;

$R_{15}$ is alkyl or haloalkyl;

X is selected from nitrogen and C—$R_{12}$;

Z is O, S(O)$_a$, or $NR_7$;

a, m, n and q are independently selected from 0, 1, and 2; and t is 0 or 2;

and veterinarily acceptable salts thereof.

In another aspect, the present invention provides a method of controlling parasites in or on an animal comprising administering orally to the animal a parasiticidally effective, substantially non-emetic amount of a 1-arylpyrazole of formula (XX):

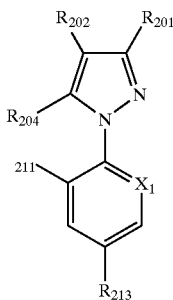

(XX)

wherein:

$R_{201}$ is cyano, C(O)alkyl, C(S)NH$_2$, alkyl, C(=NOH)NH$_2$ or C(=NNH$_2$)NH$_2$;

$R_{202}$ is S(O)$_n$R$_{203}$, C$_2$–C$_3$ alkenyl, C$_2$–C$_3$ haloalkenyl, cycloalkyl, halocycloalkyl or C$_2$–C$_3$ alkynyl;

$R_{203}$ is alkyl or haloalkyl;

$R_{204}$ is —N(R$_{205}$)C(O)CR$_{206}$R$_{207}$R$_{208}$, —N(R$_{205}$)C(O)aryl, or —N(R$_{205}$)C(O)OR$_{207}$;

$R_{205}$ is alkyl, haloalkyl, cycloalkyl, halocycloalkyl, cycloalkylalkyl, halocycloalkylalkyl, alkoxyalkyl, haloalkoxyalkyl, C$_3$–C$_5$ alkenyl, C$_3$–C$_5$ haloalkenyl, C$_3$–C$_5$ alkynyl, C$_3$–C$_5$ haloalkynyl;

$R_{206}$ is hydrogen, halogen, alkoxy, haloalkoxy, alkoxyalkyl, haloalkoxyalkyl, formyloxy, alkylcarbonyloxy, haloalkylcarbonyloxy, alkylthio, haloalkylthio, alkylsulfinyl, haloalkylsulfinyl, alkylsulfonyl, haloalkylsulfonyl, alkylamino, dialkylamino, haloalkylamino, di(haloalkyl)amino, cycloalkyloxy, halocycloalkyloxy, alkoxyalkoxy, haloalkoxyalkoxy, alkoxyalkoxyalkoxy, aryloxy, or arylalkoxy;

$R_{207}$ and $R_{208}$ are independently hydrogen, alkyl, haloalkyl, cycloalkyl, or halocycloalkyl; or R$_{207}$ and R$_{208}$ may form together with the carbon to which they are attached a 3 to 7 membered ring which additionally may contain one or more heteroatoms selected from nitrogen, oxygen and sulfur;

$X_1$ is selected from nitrogen and C—R$_{212}$;

$R_{211}$ and $R_{212}$ are independently selected from halogen, hydrogen, CN and NO$_2$;

$R_{213}$ is selected from halogen, haloalkyl, haloalkoxy, —S(O)$_k$CF$_3$, and —SF$_5$; and h and k are independently selected from 0, 1, and 2;

and veterinarily acceptable salts thereof.

DETAILED DESCRIPTION OF THE INVENTION AND PREFERRED EMBODIMENTS

By the term "veterinarily acceptable salts" is meant salts the anions of which are known and accepted in the art for the formation of salts for veterinary use. Suitable acid addition salts, e.g. formed by compounds of formulae (I) and (XX) containing a basic nitrogen atom, e.g. an amino group, include salts with inorganic acids, for example hydrochlorides, sulphates, phosphates and nitrates and salts with organic acids for example acetic acid.

Unless otherwise specified, alkyl and alkoxy groups here and throughout this specification are generally lower alkyl and alkoxy groups, that is having from one to six carbon atoms, preferably from one to four carbon atoms. Generally, the haloalkyl, haloalkoxy and alkylamino groups have from one to four carbon atoms. The haloalkyl and haloalkoxy groups can bear one or more halogen atoms; preferred groups of this type include —CF$_3$ and —OCF$_3$. Cycloalkyl groups generally have from 3 to 6 carbon atoms, preferably from 3 to 5 carbon atoms and may be substituted by one or more halogen atoms. Alkenyl, haloalkenyl, alkynyl, and haloalkynyl groups generally contain from 3 to 5 carbon atoms. By the term aryl is generally meant phenyl, pyridyl, furyl, and thiopheneyl (thienyl), each of which is optionally substituted by one or more halogen, alkyl, haloalkyl, nitro, alkoxy, haloalkoxy, hydroxy, amino, alkylamino or dialkylamino. In compounds of formula (I), by the term substituted alkyl is meant alkyl which is substituted by one or more halogen, alkoxy, haloalkoxy, amino, alkylamino, dialkylamino, cyano or —S(O)$_m$R$_{15}$; or alkyl substituted by phenyl or pyridyl each of which is optionally substituted with one or more groups selected from halogen, nitro and alkyl; wherein R$_{15}$ is alkyl or haloalkyl and m is zero, one or two. Preferably in compounds of formula (I), alkyl groups are generally substituted by from one to five halogen atoms, preferably from one to three halogen atoms. Chlorine and fluorine atoms are preferred.

The above definitions of alkyl, alkoxy and various other groups of course pertain not only to those radicals themselves but also to those portions of larger radicals.

Compounds of formula (I) wherein R$_4$ is —N=C(R$_5$)—Z—R$_6$, Z is NR$_7$ and R$_6$ represents a hydrogen atom may exist as the tautomeric double bond isomer form —NH—C(R$_5$)=N—R$_7$. It is to be understood that both such forms are embraced by the present invention.

In compounds of formula (XX) the following examples of radicals are provided:

an example of cycloalkylalkyl is cyclopropylmethyl;

an example of cycloalkoxy is cyclopropyloxy;

an example of alkoxyalkyl is CH$_3$OCH$_2$—;

an example of alkoxyalkoxy is CH$_3$OCH$_2$O—;

an example of alkoxyalkoxyalkoxy is CH$_3$OCH$_2$OCH$_2$O—;

an example of aryloxy is the phenoxy radical; and an example of the arylalkoxy radical is benzyloxy or 2-phenylethoxy.

Generally, in dialkylamino or di(haloalkyl)amino radicals, the alkyl and haloalkyl groups on nitrogen may be chosen independently of one another.

It is also to be understood that enantiomeric and diastereomeric forms of the compounds of formulae (I) and (XX) and salts thereof are embraced by the present invention. Compounds of formula (I) may be generally prepared according to known processes, for example as described in European Patent Publication 0511845 or other processes according to the knowledge of a man skilled in the art of chemical synthesis.

By the term "non-emetic" is meant a compound or composition that does not generally elicit emesis from the animal when a protective, preventative or cleaning dose is administered to the animal. By the term "emesis" is meant vomiting. Generally an emetic substance elicits emesis in less than 24 hours after administration, usually less than 8 hours, more usually less than 2 hours. By the term "substantially non-emetic" is meant that, generally, when a compound or composition of the invention is administered to a population of animals, more than 70% (or at least ⅔) of the animals are free of emesis. Preferably, more than 80%, most preferably more than 90%, of said population is free of emesis.

A preferred class of compounds of formula (I) for use in the control of parasites in animals are those wherein:

$R_1$ is cyano or alkyl;

$R_2$ is $S(O)_n R_3$;

$R_3$ is alkyl or haloalkyl;

$R_4$ is —N=C($R_5$)—Z—$R_6$;

$R_5$ is hydrogen, alkyl or haloalkyl;

Z is O, $S(O)_a$, or $NR_7$;

$R_6$ and $R_7$ are independently selected from hydrogen and unsubstituted or substituted alkyl; or $R_6$ and $R_7$ may form together with the nitrogen to which they are attached a 3 to 7 membered ring which may additionally contain one or more heteroatoms selected from oxygen, nitrogen or sulfur;

X is selected from nitrogen and C—$R_{12}$;

$R_{11}$ and $R_{12}$ are independently selected from halogen, hydrogen, CN and $NO_2$;

$R_{13}$ is selected from halogen, haloalkyl, haloalkoxy, —$S(O)_q CF_3$, and —$SF_5$;

a, n and q are independently selected from 0, 1, and 2.

Preferably $R_6$ is alkyl which is substituted by one or more halogen, alkoxy, haloalkoxy, amino, alkylamino, dialkylamino, sulfide, sulfoxide, sulfone, or phenyl or pyridyl moieties of which each phenyl or pyridyl moiety is optionally substituted with one or more groups selected from halo, nitro, and alkyl.

Preferably the method of the invention has one or more of the following features:

$R_1$ is cyano;

$R_4$ is —N=C($R_5$)—Z—$R_6$ and Z is —$NR_7$;

X is C—$R_{12}$; $R_{11}$ and $R_{12}$ represent a chlorine atom; and $R_{13}$ is $CF_3$, $OCF_3$ or —$SF_5$;

$R_{12}$ is —$S(O)_n CF_3$ and n is 0, 1, or 2.

A further preferred class of compounds of formula (I) for use in the control of parasites in animals are those wherein:

$R_1$ is cyano or alkyl; $R_4$ is —N=C($R_5$)—Z—$R_6$; and $R_5$ is hydrogen or $C_1$-$C_3$ alkyl.

The compounds of formula (I) for use in the control of parasites in animals preferably have one or more of the following features:

$R_1$ is cyano or methyl;

$R_3$ is halomethyl (preferably $CF_3$);

$R_{11}$ and $R_{12}$ each independently represent a halogen atom;

X is C—$R_{12}$;

$R_{13}$ is haloalkyl (preferably $CF_3$), haloalkoxy (preferably $OCF_3$), or —$SF_5$; or n is 0, 1 or 2 (preferably 0 or 1).

A further preferred class of compounds of formula (I) for use in the control of parasites in animals are those wherein:

$R_1$ is cyano;

$R_2$ is $S(O)_n R_3$;

$R_3$ is halomethyl;

$R_4$ is —N=C($R_5$)—Z—$R_6$;

Z is $NR_7$;

$R_5$ is hydrogen or alkyl;

$R_6$ and $R_7$ each independently represent hydrogen, alkyl, alkenyl or alkynyl; or alkyl substituted by one or more halogen, alkoxy, haloalkoxy, amino, alkylamino, dialkylamino, cyano or —$S(O)_m R_{15}$; or alkyl substituted by phenyl or pyridyl which rings are optionally substituted with one or more groups selected from halogen, nitro and alkyl;

X is selected from nitrogen and C-$R_{12}$;

$R_{11}$ and $R_{12}$ each independently represent a halogen atom;

$R_{13}$ is selected from haloalkyl, haloalkoxy and —$SF_5$;

$R_{15}$ is alkyl or haloalkyl; and m and n are independently selected from 0, 1, and 2.

A further preferred class of compounds of formula (I) for use in the control of parasites in animals is that wherein:

$R_1$ is cyano;

$R_2$ is $S(O)_n CF_3$;

$R_4$ is —N=C($R_5$)—Z—$R_6$ or —N=C($R_5$)—N($R_7$)—$R_8$;

Z is $NR_7$;

$R_5$ is hydrogen or alkyl;

$R_6$ and $R_7$ each independently represent hydrogen, alkyl, alkenyl or alkynyl; or alkyl substituted by one or more halogen, alkoxy, haloalkoxy, amino, alkylamino, dialkylamino, cyano or —$S(O)_m R_{15}$; or methyl substituted by phenyl or pyridyl which rings are optionally substituted with one or more groups selected from halogen, nitro and alkyl;

$R_8$ is alkoxy, haloalkoxy, amino, alkylamino, dialkylamino or —$S(O)_t R_{10}$;

X is selected from nitrogen and C—$R_{12}$;

$R_{10}$ and $R_{15}$ independently represent alkyl or haloalkyl;

$R_{11}$ and $R_{12}$ each represent a chlorine atom;

$R_{13}$ is $CF_3$ or —$SF_5$; and m and n are 0, 1 or 2; and t is 0 or 2.

A further preferred class of compounds of formula (I) for use in the control of parasites in animals are those wherein:

$R_1$ is cyano;

$R_2$ is $S(O)_n CF_3$;

$R_4$ is —N=C($R_5$)—Z—$R_6$;

Z is $NR_7$;

$R_5$ is hydrogen or methyl;

$R_6$ and $R_7$ each independently represent hydrogen, alkyl, alkenyl or alkynyl; or alkyl substituted by one or more halogen, alkoxy, haloalkoxy, amino, alkylamino, dialkylamino, cyano or —$S(O)_m R_{15}$; or alkyl substituted by phenyl or pyridyl which rings are optionally substituted with one or more groups selected from halogen, nitro and alkyl;

X is C—$R_{12}$;

$R_{11}$ and $R_{12}$ each represent a chlorine atom;

$R_{13}$ is $CF_3$ or —$SF_5$;

$R_{15}$ is alkyl or haloalkyl;

m is zero, one or two; and n is 0 or 1.

A further preferred class of compounds of formula (I) for use in the control of parasites in animals are those wherein:

$R_1$ is cyano;

$R_2$ is $S(O)_n CF_3$;

$R_4$ is —N=C($R_5$)—Z—$R_6$;

Z is $NR_7$;

$R_5$ and $R_7$ each represent a hydrogen atom;

$R_6$ is alkyl or haloalkyl;

X is C—$R_{12}$;

$R_{11}$ and $R_{12}$ each represent a chlorine atom;

$R_{13}$ is $CF_3$ or —$SF_5$; and n is 0.

Compounds of formula (XX) which are preferred according to the present invention are those wherein:

$R_{201}$ is cyano;

$R_{202}$ is $S(O)_hR_{203}$;

$R_{203}$ is alkyl or haloalkyl;

$R_{204}$ is —N($R_{205}$)C(O)C$R_{206}R_{207}R_{208}$;

$R_{205}$ is alkyl, haloalkyl, cycloalkyl, cycloalkylalkyl and halocycloalkylalkyl;

$R_{206}$ is alkoxy, haloalkoxy, or hydrogen;

$R_{207}$ and $R_{208}$ are independently hydrogen, alkyl, or haloalkyl; or $R_{207}$ and $R_{208}$ may form together with the carbon to which they are attached a 3 to 7 membered ring which additionally may contain one or more heteroatoms selected from nitrogen, oxygen and sulfur;

$X_1$ is selected from nitrogen and C—$R_{212}$;

$R_{211}$ and $R_{212}$ are independently selected from halogen, hydrogen, CN and $NO_2$;

$R_{213}$ is selected from halogen, haloalkyl, haloalkoxy, —$S(O)_kCF_3$, and —$SF_5$; and h and k are independently selected from 0, 1, and 2.

A preferred group of compounds of formula (XX) is that wherein the ring which is formed by $R_{207}$ and $R_{208}$ is interrupted by one or more heteroatoms, more preferably one oxygen atom.

The compounds of formula (XX) of the present invention preferably have one or more of the following features:

$R_{201}$ is cyano;

$R_{203}$ is halomethyl, preferably $CF_3$;

$R_{211}$ and $R_{212}$ are independently halogen;

$X_1$ is C—$R_{212}$;

$R_{213}$ is haloalkyl, haloalkoxy or —$SF_5$; or h is 0 or 1, or 2, preferably 0 or 1.

A preferred class of compounds is that wherein $R_{204}$ is N($R_{205}$)C(O)C$R_{206}R_{207}R_{208}$.

Another preferred class of compounds is that wherein $R_{204}$ is N($R_{205}$)C(O)aryl.

Another preferred class of compounds is that wherein $R_{204}$ is N($R_{205}$)C(O)O$R_{207}$.

Preferably $R_{205}$ is $C_1$–$C_4$ alkyl, more preferably $C_1$–$C_2$ alkyl, most preferably methyl.

Preferably $R_{206}$ is alkoxy, most preferably methoxy, ethoxy or propoxy.

Preferably $R_{207}$ and $R_{208}$ are both hydrogen.

Among the compounds which may be used in the invention some are new and hence in another aspect of the present invention there is provided a compound of formula (II):

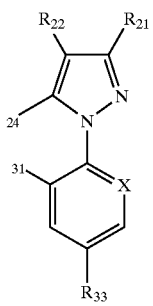

(II)

wherein:

$R_{21}$ is cyano, alkyl, haloalkyl, acetyl, —C(=S)$NH_2$, C(=NOH)$NH_2$ or C(=$NNH_2$)$NH_2$;

$R_{22}$ is $S(O)_mR_{23}$;

$R_{23}$ is alkyl or haloalkyl;

$R_{24}$ is —N=C($R_{25}$)N($R_{26}$)($R_{27}$) or —N=C($R_{25}$)—N($R_{27}$)—$R_{28}$;

$R_{25}$ represents hydrogen or alkyl; or alkyl substituted by one or more halogen, alkoxy, haloalkoxy or —$S(O)_mR_{35}$;

$R_{26}$ and $R_{27}$ each independently represent hydrogen, alkyl, alkenyl or alkynyl; or alkyl substituted by one or more halogen, alkoxy, haloalkoxy, amino, alkylamino, dialkylamino, cyano or —$S(O)_mR_{35}$; or alkyl substituted by phenyl or pyridyl which rings are optionally substituted with one or more groups selected from halogen, nitro and alkyl; wherein $R_{35}$ is alkyl or haloalkyl and m is zero, one or two;

X is selected from nitrogen and C—$R_{32}$;

$R_{28}$ is alkoxy, haloalkoxy, amino, alkylamino, dialkylamino or —$S(O)_tR_{30}$;

$R_{30}$ is alkyl or haloalkyl;

$R_{31}$ and $R_{32}$ are independently selected from halogen, hydrogen, CN and $NO_2$;

$R_{33}$ is selected from halogen, haloalkyl, haloalkoxy, —$S(O)_rCF_3$, and —$SF_5$;

m and r are independently selected from 0, 1, and 2; and t is 0 or 2; with the exclusion of the compound wherein $R_{21}$ is cyano; $R_{22}$ is —$SCF_2CH_3$; $R_{25}$ is hydrogen; X is C—$R_{32}$; $R_{26}$ and $R_{27}$ are methyl; $R_{31}$ and $R_{32}$ are chlorine; and $R_{33}$ is trifluoromethyl; and veterinarily acceptable salts thereof.

A further class of novel compounds of formula (II) are those wherein:

$R_{21}$ is cyano or methyl;

$R_{22}$ is $S(O)_mR_{23}$;

$R_{23}$ is haloalkyl;

$R_{24}$ is —N=C($R_{25}$)N($R_{26}$)($R_{27}$);

$R_{25}$ and $R_{27}$ are hydrogen or unsubstituted or substituted alkyl;

$R_{26}$ is haloalkyl;

X is selected from nitrogen and C—$R_{32}$;

$R_{31}$ and $R_{32}$ are independently selected from halogen, hydrogen, CN and $NO_2$;

$R_{33}$ is selected from halogen, haloalkyl, haloalkoxy, —$S(O)_rCF_3$, and —$SF_5$;

m and r are independently selected from 0, 1, and 2; with the exclusion of the compound wherein $R_{21}$ is cyano; $R_{22}$ is —$SCF_2CH_3$; $R_{25}$ is hydrogen; X is C—$R_{32}$; $R_{26}$ and $R_{27}$ are methyl; $R_{31}$ and $R_{32}$ are chlorine; and $R_{33}$ is trifluoromethyl.

A preferred class of novel compounds of formula (II) are those wherein:

$R_{21}$ is cyano;

$R_{22}$ is $S(O)_mR_{23}$;

$R_{23}$ is halomethyl;

$R_{24}$ is —N=C($R_{25}$)N($R_{26}$)($R_{27}$);

$R_{25}$ is hydrogen or alkyl;

$R_{26}$ and $R_{27}$ each independently represent hydrogen, alkyl, alkenyl or alkynyl; or alkyl substituted by one or more halogen, alkoxy, haloalkoxy, amino, alkylamino, dialkylamino, cyano or —$S(O)_mR_{15}$; or alkyl substituted by phenyl or pyridyl each of which is optionally substituted with one or more groups selected from halogen, nitro and alkyl; wherein $R_{15}$ is alkyl or haloalkyl and m is zero, one or two;

X is selected from nitrogen and C—$R_{32}$;

$R_{31}$ and $R_{32}$ each represent a chlorine atom;

$R_{33}$ is selected from haloalkyl, haloalkoxy and —$SF_5$;

m is selected from 0, 1, and 2.

A further preferred class of novel compounds of formula (II) are those wherein:

$R_{21}$ is cyano;

$R_{22}$ is $S(O)_mCF_3$;

$R_{24}$ is —N=C($R_{25}$)N($R_{26}$)($R_{27}$); or —N=C($R_{25}$)—N($R_{27}$)—$R_{28}$;

$R_{25}$ is hydrogen or methyl;

$R_{26}$ and $R_{27}$ each independently represent hydrogen, alkyl, alkenyl or alkynyl; or alkyl substituted by one or more halogen, alkoxy, haloalkoxy, amino, alkylamino, dialkylamino, cyano or —$S(O)_mR_{15}$; or methyl substituted by phenyl or pyridyl which rings are optionally substituted with one or more groups selected from halogen, nitro and alkyl; wherein $R_{15}$ is alkyl or haloalkyl and m is zero, one or two;

$R_{28}$ is alkoxy, haloalkoxy, amino, alkylamino, dialkylamino or —$S(O)_tR_{30}$;

X is selected from nitrogen and C—$R_{32}$;

$R_{30}$ is alkyl or haloalkyl;

$R_{31}$ and $R_{32}$ each represent a chlorine atom;

$R_{33}$ is $CF_3$ or —$SF_5$; and m is 0, 1 or 2; and t is 0 or 2.

A more preferred class of novel compounds of formula (II) are those wherein:

$R_{21}$ is cyano;

$R_{22}$ is $S(O)_mCF_3$;

$R_{24}$ is —N=C($R_{25}$)N($R_{26}$)($R_{27}$);

$R_{25}$ and $R_{27}$ each independently represent hydrogen or methyl;

$R_{26}$ represents hydrogen, alkyl, alkenyl or alkynyl; or alkyl substituted by one or more halogen, alkoxy, haloalkoxy, amino, alkylamino, dialkylamino, cyano or —$S(O)_mR_{15}$; or methyl substituted by phenyl or pyridyl which rings are optionally substituted with one or more groups selected from halogen, nitro and alkyl; wherein $R_{15}$ is alkyl or haloalkyl and m is zero, one or two;

X is selected from nitrogen and C—$R_{32}$;

$R_{31}$ and $R_{32}$ each represent a chlorine atom;

$R_{33}$ is $CF_3$ or —$SF_5$; and m is 0, 1 or 2.

An especially preferred class of novel compounds of formula (II) are those wherein:

$R_{21}$ is cyano;

$R_{22}$ is $S(O)_mCF_3$;

$R_{24}$ is —N=C($R_{25}$)N($R_{26}$)($R_{27}$);

$R_{25}$ and $R_{27}$ each represent a hydrogen atom;

$R_{26}$ is alkyl or (preferably) haloalkyl;

X is C—$R_{32}$;

$R_{31}$ and $R_{32}$ each represent a chlorine atom;

$R_{33}$ is $CF_3$ or —$SF_5$; and m is 0.

In another aspect of the present invention there is provided a compound of formula (XX) or a salt thereof as hereinbefore defined, provided that the compound is not 3-cyano-1-(2,6-dichloro-4-trifluoromethylphenyl)-5-(N-ethoxycarbonyl-N-methyl)amino-4-trifluoromethylthiopyrazole.

Most preferably, the following compounds of formulae (I) and (XX) are preferred according to the present invention as listed in Tables 1 to 13. The Compound Numbers are for identification purposes only. The following symbols are hereby defined: Me means methyl; Et means ethyl; n-Pr means n-propyl; i-Pr means isopropyl; n-Bu means n-Butyl, and n-Pent means n-Pentyl; Cy means cyclopropyl.

TABLE 1

Compounds of formula (I) wherein $R_1$ is cyano, $R_2$ is $SCF_3$, $R_{11}$ is Cl, X is C—Cl, $R_4$ is —N=C($R_5$)$ZR_6$, Z is $NR_7$, $R_7$ is H, and $R_{13}$ is $CF_3$ or $SF_5$.

| Compound Number $R_{13}$=$CF_3$ | Compound Number $R_{13}$=$SF_5$ | $R_5$ | $R_6$ |
|---|---|---|---|
| 201-1 | 201-2 | Me | Me |
| 202-1 | 202-2 | Me | Et |
| 203-1 | 203-2 | Me | n-Pr |
| 204-1 | 204-2 | Me | i-Pr |
| 205-1 | 205-2 | Me | n-Bu |
| 206-1 | 206-2 | H | H |
| 207-1 | 207-2 | H | Et |
| 208-1 | 208-2 | H | n-Pr |
| 209-1 | 209-2 | H | i-Pr |
| 210-1 | 210-2 | H | n-Bu |
| 211-1 | 211-2 | H | $CH_2CF_3$ |
| 212-1 | 212-2 | H | $(CH_2)_2CF_3$ |
| 213-1 | 213-2 | H | $CH_2OMe$ |
| 214-1 | 214-2 | H | $(CH_2)_2OCF_3$ |
| 215-1 | 215-2 | Me | $CH_2CF_3$ |
| 216-1 | 216-2 | Me | $(CH_2)_2CF_3$ |
| 217-1 | 217-2 | Me | $(CH_2)_2OMe$ |
| 218-1 | 218-2 | Me | $(CH_2)_2NMe_2$ |

TABLE 2

Compounds of formula (I) wherein $R_1$ is cyano; $R_{11}$ is Cl; $R_4$ is —N=C($R_5$)$ZR_6$ and Z is $NR_7$.

| Cmpd No. | $R_2$ | $R_5$ | $R_6$ | $R_7$ | X | $R_{13}$ |
|---|---|---|---|---|---|---|
| 219 | $SCF_3$ | H | $CH_3$ | $CH_3$ | C—Cl | $CF_3$ |
| 220 | $SO_2CF_3$ | H | $CH_3$ | $CH_3$ | C—Cl | $CF_3$ |
| 221 | $SCF_3$ | H | $CH_2CN$ | H | C—Cl | $CF_3$ |
| 222 | $SCF_3$ | H | $CH_3$ | H | C—Cl | $CF_3$ |
| 223 | $SOCF_3$ | H | $CH_2Ph$ | H | C—Cl | $CF_3$ |
| 224 | $SCF_3$ | H | $CH_2Ph$ | H | C—Cl | $CF_3$ |
| 225 | $SOCF_3$ | H | $CH_3$ | H | C—Cl | $CF_3$ |
| 226 | $SOCF_3$ | H | $CH_3$ | H | C—Cl | $CF_3$ |
| 227 | $SOCF_3$ | H | $CH_2CF_3$ | H | C—Cl | $CF_3$ |
| 228 | $SO_2CF_3$ | H | 2-propynyl | H | C—Cl | $CF_3$ |
| 229 | $SO_2CF_3$ | H | $CH_2Ph$ | H | C—Cl | $CF_3$ |
| 230 | $SO_2CF_3$ | H | $CH_2CF_3$ | H | C—Cl | $CF_3$ |
| 231 | $SOCF_3$ | H | $CH_3$ | $CH_3$ | C—Cl | $CF_3$ |
| 232 | $SCF_3$ | H | $CH_2CF_3$ | H | C—Cl | $CF_3$ |
| 233 | $SCF_3$ | H | $CH_2CF_3$ | H | C—Cl | $CF_3$ |
| 234 | $SCF_3$ | H | 2-propenyl | H | C—Cl | $CF_3$ |
| 235 | $SCF_3$ | H | 2-propynyl | H | C—Cl | $CF_3$ |
| 236 | $SOCF_3$ | H | 2-propynyl | H | C—Cl | $CF_3$ |
| 237 | $SCF_3$ | H | $CH_2OEt$ | H | N | $CF_3$ |
| 238 | $SCF_3$ | H | $CH_2OCH_2CF_3$ | $CH_3$ | C—Cl | $CF_3$ |
| 239 | $SO_2CF_3$ | H | $CH_2CF_3$ | $CH_3$ | C—Cl | $SF_5$ |
| 240 | $SCF_3$ | H | $CH_2CF_3$ | H | N | $SF_5$ |
| 241 | $SOCF_3$ | H | $CH_2CH_2CF_3$ | H | C—Cl | $CF_3$ |
| 242 | $SO_2CF_3$ | H | $(CH_2)_3CF_3$ | H | C—Cl | $CF_3$ |
| 243 | $SCF_3$ | H | $(CH_2)_2N(CH_3)_2$ | H | C—Cl | $CF_3$ |
| 244 | $SO_2CF_3$ | $CH_3$ | $CH_2$(4-Cl Ph) | H | C—Cl | $CF_3$ |
| 245 | $SCF_3$ | H | $CH_2SO_2CF_3$ | H | C—Cl | $CF_3$ |
| 246 | $SCF_3$ | H | $CH_2$(4-pyridyl) | H | C—Cl | $CF_3$ |
| 247 | $SCF_3$ | H | $CH_2$(3-$NO_2$ Ph) | H | C—Cl | $CF_3$ |

TABLE 2-continued

Compounds of formula (I) wherein $R_1$ is cyano; $R_{11}$ is Cl; $R_4$ is $-N=C(R_5)ZR_6$ and Z is $NR_7$.

| Cmpd No. | $R_2$ | $R_5$ | $R_6$ | $R_7$ | X | $R_{13}$ |
|---|---|---|---|---|---|---|
| 248 | $SCF_3$ | H | $CH_2CH_2SCH_3$ | H | C—Cl | $CF_3$ |
| 249 | $SOCF_3$ | H | $CH_2CF_3$ | $CH_3$ | C—Cl | $CF_3$ |

Note:
Compounds 225 and 226 are regioisomers of the same molecular formula. In one, $R_5$ is H and $R_6$ is methyl; and in the other, $R_5$ is methyl and $R_6$ is H, but they cannot be distinguished.
Also note:
Compound number 232 is the acetate salt, and compound number 233 is the citrate salt.

TABLE 3

Compounds of formula (I) wherein $R_1$ is cyano; $R_{11}$ is Cl; and $R_4$ is $-N=C(R_5)-N(R_7)-R_8$.

| Cmpd No. | $R_2$ | $R_5$ | $R_8$ | $R_7$ | X | $R_{13}$ |
|---|---|---|---|---|---|---|
| 250 | $SCF_3$ | H | OEt | H | C—Cl | $CF_3$ |
| 251 | $SCF_3$ | H | $NHCH_3$ | H | C—Cl | $CF_3$ |
| 252 | $SCF_3$ | H | $NHCH_3$ | $CH_3$ | C—Cl | $CF_3$ |
| 253 | $SCF_3$ | H | $OCH_2CF_3$ | H | C—Cl | $CF_3$ |
| 254 | $SCF_3$ | H | $N(CH_3)_2$ | H | N | $SF_5$ |
| 255 | $SCF_3$ | H | $NH_2$ | H | C—Cl | $CF_3$ |
| 256 | $SCF_3$ | H | S-nPr | H | C—Cl | $CF_3$ |
| 257 | $SO_2CF_3$ | Et | S-nPr | H | C—Cl | $SF_5$ |
| 258 | $SCF_3$ | H | $SO_2CH_3$ | H | C—Cl | $CF_3$ |

The following compounds of formula (XX) are preferred according to the present invention as listed in Tables 4–12.

TABLE 4

Compounds of formula (XX) wherein $R_{201}$ is cyano; $R_{202}$ is $SCF_3$; $R_{204}$ is $N(R_{205})C(O)CR_{206}R_{207}R_{208}$; $R_{207}$ and $R_{208}$=H; $R_{211}$ is Cl, $X_1$ is C—Cl, and $R_{213}$ is $CF_3$ or $SF_5$.

| Compound Number ($R_{213}$=$CF_3$) | Compound Number ($R_{213}$=$SF_5$) | $R_{205}$ | $R_{206}$ |
|---|---|---|---|
| 1-1 | 1-2 | Me | H |
| 2-1 | 2-2 | Me | OMe |
| 3-1 | 3-2 | Me | OEt |
| 4-1 | 4-2 | Me | O-i-Pr |
| 5-1 | 5-2 | Me | O-n-Bu |
| 6-1 | 6-2 | Et | H |
| 7-1 | 7-2 | Et | OMe |
| 8-1 | 8-2 | Et | OEt |
| 9-1 | 9-2 | Et | O-i-Pr |
| 10-1 | 10-2 | Et | O-n-Bu |
| 11-1 | 11-2 | n-Pr | H |
| 12-1 | 12-2 | n-Pr | OMe |
| 13-1 | 13-2 | n-Pr | OEt |
| 14-1 | 14-2 | n-Pr | O-i-Pr |
| 15-1 | 15-2 | n-Pr | O-n-Bu |
| 16-1 | 16-2 | i-Pr | H |
| 17-1 | 17-2 | i-Pr | OMe |
| 18-1 | 18-2 | i-Pr | OEt |
| 19-1 | 19-2 | i-Pr | O-i-Pr |
| 20-1 | 20-2 | i-Pr | O-n-Bu |
| 21-1 | 21-2 | n-Bu | H |
| 22-1 | 22-2 | n-Bu | OMe |
| 23-1 | 23-2 | n-Bu | OEt |
| 24-1 | 24-2 | n-Bu | O-i-Pr |
| 25-1 | 25-2 | n-Bu | O-n-Bu |
| 26-1 | 26-2 | $CH_2Cy$ | H |
| 27-1 | 27-2 | $CH_2Cy$ | OMe |
| 28-1 | 28-2 | $CH_2Cy$ | OEt |

TABLE 4-continued

Compounds of formula (XX) wherein $R_{201}$ is cyano; $R_{202}$ is $SCF_3$; $R_{204}$ is $N(R_{205})C(O)CR_{206}R_{207}R_{208}$; $R_{207}$ and $R_{208}$=H; $R_{211}$ is Cl, $X_1$ is C—Cl, and $R_{213}$ is $CF_3$ or $SF_5$.

| Compound Number ($R_{213}$=$CF_3$) | Compound Number ($R_{213}$=$SF_5$) | $R_{205}$ | $R_{206}$ |
|---|---|---|---|
| 29-1 | 29-2 | $CH_2Cy$ | O-i-Pr |
| 30-1 | 30-2 | $CH_2Cy$ | O-n-Bu |
| 31-1 | 31-2 | $CH_2CCH$ | H |
| 32-1 | 32-2 | $CH_2CCH$ | OMe |
| 33-1 | 33-2 | $CH_2CCH$ | OEt |
| 34-1 | 34-2 | $CH_2CCH$ | O-i-Pr |
| 35-1 | 35-2 | $CH_2CCH$ | O-n-Bu |
| 36-1 | 36-2 | Me | OAc |
| 37-1 | 37-2 | Me | $CH_2OMe$ |
| 38-1 | 38-2 | Me | $CH_2OEt$ |
| 39-1 | 39-2 | Me | O-i-Pr |
| 40-1 | 40-2 | Me | O-n-Bu |
| 41-1 | 41-2 | Me | $OCH_2CF_3$ |

TABLE 5

Compounds of formula (XX) wherein $R_{201}$ is cyano; $R_{202}$ is $S(O)CF_3$; $R_{204}$ is $N(R_{205})C(O)CR_{206}R_{207}R_{208}$; $R_{207}$ and $R_{208}$=H; $R_{211}$ is Cl, $X_1$ is C—Cl, and $R_{213}$ is $CF_3$ or $SF_5$.

| Compound Number ($R_{213}$=$CF_3$) | Compound Number ($R_{213}$=$SF_5$) | $R_{205}$ | $R_{206}$ |
|---|---|---|---|
| 1-3 | 1-4 | Me | H |
| 2-3 | 2-4 | Me | OMe |
| 3-3 | 3-4 | Me | OEt |
| 4-3 | 4-4 | Me | O-i-Pr |
| 5-3 | 5-4 | Me | O-n-Bu |
| 6-3 | 6-4 | Et | H |
| 7-3 | 7-4 | Et | OMe |
| 8-3 | 8-4 | Et | OEt |
| 9-3 | 9-4 | Et | O-i-Pr |
| 10-3 | 10-4 | Et | O-n-Bu |
| 11-3 | 11-4 | n-Pr | H |
| 12-3 | 12-4 | n-Pr | OMe |
| 13-3 | 13-4 | n-Pr | OEt |
| 14-3 | 14-4 | n-Pr | O-i-Pr |
| 15-3 | 15-4 | n-Pr | O-n-Bu |
| 16-3 | 16-4 | i-Pr | H |
| 17-3 | 17-4 | i-Pr | OMe |
| 18-3 | 18-4 | i-Pr | OEt |
| 19-3 | 19-4 | i-Pr | O-i-Pr |
| 20-3 | 20-4 | i-Pr | O-n-Bu |
| 21-3 | 21-4 | n-Bu | H |
| 22-3 | 22-4 | n-Bu | OMe |
| 23-3 | 23-4 | n-Bu | OEt |
| 24-3 | 24-4 | n-Bu | O-i-Pr |
| 25-3 | 25-4 | n-Bu | O-n-Bu |
| 26-3 | 26-4 | $CH_2Cy$ | H |
| 27-3 | 27-4 | $CH_2Cy$ | OMe |
| 28-3 | 28-4 | $CH_2Cy$ | OEt |
| 29-3 | 29-4 | $CH_2Cy$ | O-i-Pr |
| 30-3 | 30-4 | $CH_2Cy$ | O-n-Bu |
| 31-3 | 31-4 | $CH_2CCH$ | H |
| 32-3 | 32-4 | $CH_2CCH$ | OMe |
| 33-3 | 33-4 | $CH_2CCH$ | OEt |
| 34-3 | 34-4 | $CH_2CCH$ | O-i-Pr |
| 35-3 | 35-4 | $CH_2CCH$ | O-n-Bu |
| 36-3 | 36-4 | Me | OAc |
| 37-3 | 37-4 | Me | $CH_2OMe$ |
| 38-3 | 38-4 | Me | $CH_2OEt$ |
| 39-3 | 39-4 | Me | O-i-Pr |
| 40-3 | 40-4 | Me | O-n-Bu |
| 41-3 | 41-4 | Me | $OCH_2CF_3$ |

Compound 3-3 was separated into its enantiomers (R)3-3 and (S)3-3.

TABLE 6

Compounds of formula (XX) wherein $R_{201}$ is cyano; $R_{202}$ is $S(O)_2CF_3$; $R_{204}$ is $N(R_{205})C(O)CR_{206}R_{207}R_{208}$; $R_{207}$ and $R_{208}$=H; $R_{211}$ is Cl, $X_1$ is C—Cl, and $R_{213}$ is $CF_3$ or $SF_5$.

| Compound Number ($R_{213}$=$CF_3$) | Compound Number ($R_{213}$=$SF_5$) | $R_{205}$ | $R_{206}$ |
|---|---|---|---|
| 1-5 | 1-6 | Me | H |
| 2-5 | 2-6 | Me | OMe |
| 3-5 | 3-6 | Me | OEt |
| 4-5 | 4-6 | Me | O-i-Pr |
| 5-5 | 5-6 | Me | O-n-Bu |
| 6-5 | 6-6 | Et | H |
| 7-5 | 7-6 | Et | OMe |
| 8-5 | 8-6 | Et | OEt |
| 9-5 | 9-6 | Et | O-i-Pr |
| 10-5 | 10-6 | Et | O-n-Bu |
| 11-5 | 11-6 | n-Pr | H |
| 12-5 | 12-6 | n-Pr | OMe |
| 13-5 | 13-6 | n-Pr | OEt |
| 14-5 | 14-6 | n-Pr | O-i-Pr |
| 15-5 | 15-6 | n-Pr | O-n-Bu |
| 16-5 | 16-6 | i-Pr | H |
| 17-5 | 17-6 | i-Pr | OMe |
| 18-5 | 18-6 | i-Pr | OEt |
| 19-5 | 19-6 | i-Pr | O-i-Pr |
| 20-5 | 20-6 | i-Pr | O-n-Bu |
| 21-5 | 21-6 | n-Bu | H |
| 22-5 | 22-6 | n-Bu | OMe |
| 23-5 | 23-6 | n-Bu | OEt |
| 24-5 | 24-6 | n-Bu | O-i-Pr |
| 25-5 | 25-6 | n-Bu | O-n-Bu |
| 26-5 | 26-6 | $CH_2Cy$ | H |
| 27-5 | 27-6 | $CH_2Cy$ | OMe |
| 28-5 | 28-6 | $CH_2Cy$ | OEt |
| 29-5 | 29-6 | $CH_2Cy$ | O-i-Pr |
| 30-5 | 30-6 | $CH_2Cy$ | O-n-Bu |
| 31-5 | 31-6 | $CH_2CCH$ | H |
| 32-5 | 32-6 | $CH_2CCH$ | OMe |
| 33-5 | 33-6 | $CH_2CCH$ | OEt |
| 34-5 | 34-6 | $CH_2CCH$ | O-i-Pr |
| 35-5 | 35-6 | $CH_2CCH$ | O-n-Bu |
| 36-5 | 36-6 | Me | OAc |
| 37-5 | 37-6 | Me | $CH_2OMe$ |
| 38-5 | 38-6 | Me | $CH_2OEt$ |
| 39-5 | 39-6 | Me | O-i-Pr |
| 40-5 | 40-6 | Me | O-n-Bu |
| 41-5 | 41-6 | Me | $OCH_2CF_3$ |

TABLE 7

Compounds of formula (XX) wherein $R_{201}$ is cyano; $R_{202}$ is $SCF_3$; $R_{204}$ is $N(R_{205})C(O)CR_{206}R_{207}R_{208}$; $R_{211}$ is Cl; $X_1$ is C—Cl; and $R_{213}$ is $CF_3$ or $SF_5$.

| Compound Number ($R_{213}$=$CF_3$) | Compound Number ($R_{213}$=$SF_5$) | $R_{205}$ | $R_{206}$ | $R_{207}$, $R_{208}$ |
|---|---|---|---|---|
| 1-7 | 1-8 | Me | H | —$CH_2CH_2CH_2O$— |
| 2-7 | 2-8 | Et | H | —$CH_2CH_2CH_2O$— |
| 3-7 | 3-8 | i-Pr | H | —$CH_2CH_2CH_2O$— |
| 4-7 | 4-8 | n-Pr | H | —$CH_2CH_2CH_2O$— |
| 5-7 | 5-8 | n-Bu | H | —$CH_2CH_2CH_2O$— |
| 6-7 | 6-8 | Cy | H | —$CH_2CH_2CH_2O$— |
| 7-7 | 7-8 | $CH_2Cy$ | H | —$CH_2CH_2CH_2O$— |
| (S)1-7 | — | Me | H | —$CH_2CH_2CH_2O$— |
| (R)1-7 | — | Me | H | —$CH_2CH_2CH_2O$— |

Compound 1-7 was separated into its enantiomers, called (R)1-7 and (S)1-7.

TABLE 8

Compounds of formula (XX) wherein $R_{201}$ is cyano; $R_{202}$ is $S(O)CF_3$; $R_{204}$ is $N(R_{205})C(O)CR_{206}R_{207}R_{208}$; $R_{211}$ is Cl, $X_1$ is C—Cl; and $R_{213}$ is $CF_3$ or $SF_5$.

| Compound Number ($R_{213}$=$CF_3$) | Compound Number ($R_{213}$=$SF_5$) | $R_{205}$ | $R_{206}$ | $R_{207}$, $R_{208}$ |
|---|---|---|---|---|
| 1-9 | 1-10 | Me | H | —$CH_2CH_2CH_2O$— |
| 2-9 | 2-10 | Et | H | —$CH_2CH_2CH_2O$— |
| 3-9 | 3-10 | i-Pr | H | —$CH_2CH_2CH_2O$— |
| 4-9 | 4-10 | n-Pr | H | —$CH_2CH_2CH_2O$— |
| 5-9 | 5-10 | n-Bu | H | —$CH_2CH_2CH_2O$— |
| 6-9 | 6-10 | $CH_2Cy$ | H | —$CH_2CH_2CH_2O$— |
| 7-9 | 7-10 | Cy | H | —$CH_2CH_2CH_2O$— |

Compound 1-9 was separated into its diastereomers, (R,R)1-9, (S,R)1-9, (S,S)1-9, (R,S)1-9. The first designation of absolute configuration refers to the configuration of the sulfoxide moiety, the second to the chiral carbon.

TABLE 9

Compounds of formula (XX) wherein $R_{201}$ is cyano; $R_{202}$ is $S(O)_2CF_3$; $R_{204}$ is $N(R_{205})C(O)CR_{206}R_{207}R_{208}$; $R_{211}$ is Cl; $X_1$ is C—Cl; and $R_{213}$ is $CF_3$ or $SF_5$.

| Compound Number ($R_{213}$=$CF_3$) | Compound Number ($R_{213}$=$SF_5$) | $R_{205}$ | $R_{206}$ | $R_{207}$, $R_{208}$ |
|---|---|---|---|---|
| 1-11 | 1-12A | Me | H | —$CH_2CH_2CH_2O$— |
| 2-11 | 2-12A | Et | H | —$CH_2CH_2CH_2O$— |
| 3-11 | 3-12A | i-Pr | H | —$CH_2CH_2CH_2O$— |
| 4-11 | 4-12A | n-Pr | H | —$CH_2CH_2CH_2O$— |
| 5-11 | 5-12A | n-Bu | H | —$CH_2CH_2CH_2O$— |
| 6-11 | 6-12A | Cy | H | —$CH_2CH_2CH_2O$— |
| 7-11 | 7-12A | $CH_2Cy$ | H | —$CH_2CH_2CH_2O$— |

Compound 1-11 was also separated into its diastereomers, (R)1-11 and (S)1-11.

TABLE 10

Compounds of formula (XX) wherein $R_{201}$ is cyano; $R_{204}$ is $N(R_{205})C(O)CR_{206}R_{207}R_{208}$; $R_{207}$ and $R_{208}$ are H; $R_{211}$ is Cl, $X_1$ is C—Cl; and $R_{213}$ is $CF_3$ or $SF_5$.

| Compound Number ($R_{213}$=$CF_3$) | Compound Number ($R_{213}$=$SF_5$) | $R_{205}$ | $R_{206}$ |
|---|---|---|---|
| $R_{202}$=$SCF_3$ | | | |
| 1-12 | 1-13 | Cy | H |
| 2-12 | 2-13 | Cy | OMe |
| 3-12 | 3-13 | Cy | OEt |
| 4-12 | 4-13 | Cy | i-O-Pr |
| 5-12 | 5-13 | Cy | O-n-Bu |
| $R_{202}$=$S(O)CF_3$ | | | |
| 6-12 | 6-13 | Cy | H |
| 7-12 | 7-13 | Cy | OMe |
| 8-12 | 8-13 | Cy | OEt |
| 9-12 | 9-13 | Cy | O-i-Pr |
| 10-12 | 10-13 | Cy | O-n-Bu |
| $R_{202}$=$S(O)_2CF_3$ | | | |
| 11-12 | 11-13 | Cy | H |
| 12-12 | 12-13 | Cy | OMe |
| 13-12 | 13-13 | Cy | OEt |
| 14-12 | 14-13 | Cy | O-i-Pr |
| 15-12 | 15-13 | Cy | O-n-Bu |

TABLE 11

Compounds of formula (XX) wherein $R_{201}$ is cyano; $R_{204}$ is $-N(R_{205})C(O)OR_{207}$; $R_{211}$ is Cl; $X_1$ is C—Cl, and $R_{213}$ is $CF_3$ or $SF_5$.

| Compound Number ($R_{213}=CF_3$) | Compound Number ($R_{213}=SF_5$) | $R_{205}$ | $R_{207}$ |
|---|---|---|---|
| \multicolumn{4}{c}{$R_{202}$ is $SCF_3$} | | | |
| 67-1 | 67-2 | Me | Me |
| 68-1 | 68-2 | Me | Et |
| 69-1 | 69-2 | Me | i-Pr |
| 70-1 | 70-2 | Me | n-Pr |
| 71-1 | 71-2 | Et | Me |
| 72-1 | 72-2 | Et | Et |
| 73-1 | 73-2 | Et | i-Pr |
| 74-1 | 74-2 | Et | n-Pr |
| 75-1 | 75-2 | n-Pr | Me |
| 76-1 | 76-2 | n-Pr | Et |
| 77-1 | 77-2 | n-Pr | i-Pr |
| 78-1 | 78-2 | n-Pr | n-Pr |
| 79-1 | 79-2 | i-Pr | Me |
| 80-1 | 80-2 | i-Pr | Et |
| 81-1 | 81-2 | i-Pr | i-Pr |
| 82-1 | 82-2 | i-Pr | n-Pr |
| \multicolumn{4}{c}{$R_{202}$ is $S(O)CF_3$} | | | |
| 83-1 | 83-2 | Me | Me |
| 84-1 | 84-2 | Me | Et |
| 85-1 | 85-2 | Me | i-Pr |
| 86-1 | 86-2 | Me | n-Pr |
| 87-1 | 87-2 | Et | Me |
| 88-1 | 88-2 | Et | Et |
| 89-1 | 89-2 | Et | i-Pr |
| 90-1 | 90-2 | Et | n-Pr |
| 91-1 | 91-2 | n-Pr | Me |
| 92-1 | 92-2 | n-Pr | Et |
| 93-1 | 93-2 | n-Pr | i-Pr |
| 94-1 | 94-2 | n-Pr | n-Pr |
| 95-1 | 95-2 | i-Pr | Me |
| 96-1 | 96-2 | i-Pr | Et |
| 97-1 | 97-2 | i-Pr | i-Pr |
| 98-1 | 98-2 | i-Pr | n-Pr |
| \multicolumn{4}{c}{$R_{202}$ is $S(O)_2CF_3$} | | | |
| 99-1 | 99-2 | Me | Me |
| 100-1 | 100-2 | Me | Et |
| 101-1 | 101-2 | Me | i-Pr |
| 102-1 | 102-2 | Me | n-Pr |
| 103-1 | 103-2 | Et | Me |
| 104-1 | 104-2 | Et | Et |
| 105-1 | 105-2 | Et | i-Pr |
| 106-1 | 106-2 | Et | n-Pr |
| 107-1 | 107-2 | n-Pr | Me |
| 108-1 | 108-2 | n-Pr | Et |
| 109-1 | 109-2 | n-Pr | i-Pr |
| 110-1 | 110-2 | n-Pr | n-Pr |
| 111-1 | 111-2 | i-Pr | Me |
| 112-1 | 112-2 | i-Pr | Et |
| 113-1 | 113-2 | i-Pr | i-Pr |
| 114-1 | 114-2 | i-Pr | n-Pr |

TABLE 12

Compounds of formula (XX) wherein $R_{201}$ is cyano; $R_{202}$ is $S(O)_hCF_3$; $R_{204}$ is $N(R_{205})C(O)CR_{206}R_{207}R_{208}$; $R_{211}$ is Cl; $X_1$ is C—Cl, and $R_{213}$ is $CF_3$ or $SF_5$.

| Compound Number ($R_{213}=CF_3$) | Compound Number ($R_{213}=SF_5$) | h | $R_{205}$ | $R_{206}$ | $R_{207}$ | $R_{208}$ |
|---|---|---|---|---|---|---|
| 115-1 | 115-2 | 0 | Me | H | Me | Me |
| 116-1 | 116-2 | 0 | Me | OEt | H | Me |
| 117-1 | 117-2 | 0 | Me | H | —CH$_2$CH$_2$— | |
| 118-1 | 118-2 | 0 | Me | OMe | H | Me |
| 119-1 | 119-2 | 0 | Me | OEt | Me | Me |
| 120-1 | 120-2 | 2 | Me | OCH$_2$CH$_2$OMe | H | H |
| 121-1 | 121-2 | 0 | Me | H | —CH$_2$CH$_2$CH$_2$CH$_2$O— | |
| 122-1 | 122-2 | 1 | Me | OEt | H | Me |
| 123-1 | 123-2 | 0 | Me | H | H | Me |
| 124-1 | 124-2 | 0 | Me | H | H | Et |

TABLE 13

Compounds of formula (XX) wherein $R_{201}$ is cyano; $R_{202}$ is $S(O)_hCF_3$; $R_{204}$ is $N(R_{205})C(O)aryl$; $R_{205}$ is $CH_3$; $R_{211}$ is Cl; $X_1$ is C—Cl, and $R_{213}$ is $CF_3$ or $SF_5$.

Within this table the following symbols are defined:
Ph means phenyl;
Fu means furyl;
Th means the thiophene radical, i.e., thienyl;
Pyr means pyridyl.

| Compound Number ($R_{213}=CF_3$) | Compound Number ($R_{213}=SF_5$) | Aryl |
|---|---|---|
| \multicolumn{3}{c}{$R_{202}$ is $SCF_3$} | | |
| 125-1 | 125-2 | Ph |
| 126-1 | 126-2 | 4-OMe—Ph |
| 127-1 | 127-2 | 4-CF$_3$—Ph |
| 128-1 | 128-2 | 2-Th |
| 129-1 | 129-2 | 3-Th |
| 130-1 | 130-2 | 2-Fu |
| 131-1 | 131-2 | 3-Fu |
| 132-1 | 132-2 | 2-Pyr |
| 133-1 | 133-2 | 3-Pyr |
| 134-1 | 134-2 | 4-Pyr |
| 135-1 | 135-2 | 6-Cl-2-Pyr |
| 136-1 | 136-2 | 6-CF$_3$-2-Pyr |
| 137-1 | 137-2 | 5-Cl-2-Fu |
| 138-1 | 138-2 | 5-CF$_3$-2-Fu |
| 139-1 | 139-2 | 5-OMe-2-Th |
| 140-1 | 140-2 | 5-CF$_3$-2-Th |
| \multicolumn{3}{c}{$R_{202}$ is $S(O)CF_3$} | | |
| 125-3 | 125-4 | Ph |
| 126-3 | 126-4 | 4-OMe—Ph |
| 127-3 | 127-4 | 4-CF$_3$—Ph |
| 128-3 | 128-4 | 2-Th |
| 129-3 | 129-4 | 3-Th |
| 130-3 | 130-4 | 2-Fu |
| 131-3 | 131-4 | 3-Fu |
| 132-3 | 132-4 | 2-Pyr |
| 133-3 | 133-4 | 3-Pyr |
| 134-3 | 134-4 | 4-Pyr |
| 135-3 | 135-4 | 6-Cl-2-Pyr |
| 136-3 | 136-4 | 6-CF$_3$-2-Pyr |
| 137-3 | 137-4 | 5-Cl-2-Fu |
| 138-3 | 138-4 | 5-CF$_3$-2-Fu |
| 139-3 | 139-4 | 5-OMe-2-Th |
| 140-3 | 140-4 | 5-CF$_3$-2-Th |
| \multicolumn{3}{c}{$R_{202}$ is $S(O)_2CF_3$} | | |
| 125-5 | 125-6 | Ph |
| 126-5 | 126-6 | 4-OMe—Ph |
| 127-5 | 127-6 | 4-CF$_3$—Ph |
| 128-5 | 128-6 | 2-Th |
| 129-5 | 129-6 | 3-Th |
| 130-5 | 130-6 | 2-Fu |

TABLE 13-continued

Compounds of formula (XX) wherein $R_{201}$ is cyano; $R_{202}$ is $S(O)_b CF_3$; $R_{204}$ is $N(R_{205})C(O)aryl$; $R_{205}$ is $CH_3$; $R_{211}$ is Cl; $X_1$ is C—Cl, and $R_{213}$ is $CF_3$ or $SF_5$.
Within this table the following symbols are defined:
Ph means phenyl;
Fu means furyl;
Th means the thiophene radical, i.e., thienyl;
Pyr means pyridyl.

| Compound Number ($R_{213}$=$CF_3$) | Compound Number ($R_{213}$=$SF_5$) | Aryl |
| --- | --- | --- |
| 131-5 | 131-6 | 3-Fu |
| 132-5 | 132-6 | 2-Pyr |
| 133-5 | 133-6 | 3-Pyr |
| 134-5 | 134-6 | 4-Pyr |
| 135-5 | 135-6 | 6-Cl-2-Pyr |
| 136-5 | 136-6 | 6-$CF_3$-2-Pyr |
| 137-5 | 137-6 | 5-Cl-2-Fu |
| 138-5 | 138-6 | 5-$CF_3$-2-Fu |
| 139-5 | 139-6 | 5-OMe-2-Th |
| 140-5 | 140-6 | 5-$CF_3$-2-Th |

The present invention also relates to a composition comprising a parasiticidally effective, substantially non-emetic amount of a compound of formula (I) or a salt thereof or a compound of formula (XX) or a salt thereof and an acceptable carrier. Acceptable carriers for the use of the compounds are generally known to the skilled addressee concerned with arthropod pest control in animals, particularly domestic animals, most preferably dogs or cats.

The compositions which can be used in the invention can comprise generally from about 0.001 to 95% of the compound of formula (I) or a salt thereof or a compound of formula (XX) or a salt thereof. The remainder of the composition up to 100% comprises a carrier as well as generally various additives. In this specification and the accompanying claims, percentages are by weight.

The diluted liquid formulations generally comprise from about 0.001 to about 3% of compound of formula (I) or a salt thereof or compound of formula (XX) or a salt thereof, preferably from about 0.1 to about 0.5%.

Solid formulations generally comprise from about 0.1 to about 8% of compound of formula (I) or a salt thereof or a compound of formula (XX) or a salt thereof, preferably from about 0.5 to about 1.5%.

Compositions for oral administration comprise one or more of the compounds of general formula (I) or salts thereof or compounds of formula (XX) or salts thereof in association with veterinarily acceptable carriers or coatings and include, for example, tablets, pills, capsules, gels, drenches, medicated feeds, medicated drinking water, medicated dietary supplements, slow-release boluses or other slow-release devices intended to be retained within the gastrointestinal tract. Any of these may incorporate the active ingredients contained within micro-capsules or coated with acid-labile or alkali-labile or other pharmaceutically acceptable enteric coatings. Feed premixes or concentrates containing compounds of the present invention for use in preparation of medicated diets, drinking water or other materials for consumption by animals may also be used. In a highly preferred embodiment, the compositions are administered postprandially, preferably from just after a meal to 2 hours after the meal.

In a highly preferred embodiment, there is provided a product which is readily chewed by the animal and which product does generally not allow human contamination when the product is provided to the animal by hand.

The compounds of general formula (I) or salts thereof or compounds of formula (XX) or salts thereof may be administered before, during or after meals. The compounds of general formula (I) or salts thereof or compounds of formula (XX) or salts thereof may be mixed with a carrier and/or a foodstuff.

According to the present invention the compound of formula (I) or a salt thereof or a compound of formula (XX) or a salt thereof formula (I) is administered orally in a dose to the animal in a dose range generally from 0.1 to 500 mg/kg of the compound of formula (I) or a salt thereof or a compound of formula (XX) or a salt thereof (I) per kilogram of animal body weight (mg/kg), preferably from 1 to 100 mg/kg, more preferably from 1 to 50 mg/kg, even more preferably from 2 to 25 mg/kg, most preferably from 3 to 15 mg/kg.

According to the present invention, the frequency of treatment of the animal, preferably the domestic animal to be treated by the compound of formula (I) or a salt thereof or a compound of formula (XX) or a salt thereof, is generally from about once per week to about once per year, preferably from about once every two weeks to about once every six months, more preferably from about once every two weeks to once every three months, even more preferably from about once every two weeks to about once every six weeks, and most preferably from about once every three weeks to about once every five weeks. Most highly desirable treatment is about once a month.

Generally the animal to be treated is a domestic animal, preferably a domestic companion animal. More preferably the animal to be treated is a dog and/or a cat.

The compounds of the invention may be administered most advantageously with another parasiticidally effective material, such as an endoparasiticide, and/or an ectoparasiticide, and/or an endectoparasiticide. For example, such compounds include, namely macrocyclic lactones such as avermectins or milbemycins e.g., ivermectin; pyratel (generally administered as pyrantel pamoate) or an insect growth regulator such as lufenuron or methoprene.

By the term "parasites" as used in the specification and claims is meant endoparasites and ectoparasites of warm-blooded animals, particularly ectoparasites. Preferably, fleas and/or ticks are controlled by the method of the present invention.

Illustrative of specific parasites of various host animals which may be controlled by the method of this invention include arthropods such as:

Mites: Mesostigmata spp. e.g. mesostigmatids such as the chicken mite, *Dermanyssus gallinae*; itch or scab mites such as Sarcoptidae spp. for example *Sarcoptes scabiei*; mange mites such as Psoroptidae spp. including *Chorioptes bovis* and *Psoroptes ovis*; chiggers e.g. Trombiculidae spp. for example the north american chigger, *Trombicula alfreddugesi;*

Ticks: e.g., soft-bodied ticks including Argasidae spp. for example Argas spp. and Ornithodoros spp.; hard-bodied ticks including Ixodidae spp., for example *Rhipicephalus sanguineus*, and Boophilus spp.;

Lice: sucking lice, e.g., Menopon spp. and Bovicola spp.; biting lice, e.g., Haematopinus spp., Linognathus spp. and Solenopotes spp.;

Fleas: e.g., Ctenocephalides spp., such as dog flea (*Ctenocephalides canis*) and cat flea (*Ctenocephalides*

*felis*); Xenopsylla spp. such as oriental rat flea (*Xenopsylla cheopis*); and Pulex spp. such as human flea (*Pulex irritans*);

True bugs: e.g., Cimicidae or including the common bed bug (*Cimex lectularius*); Triatominae spp. including triatomid bugs also known as kissing bugs; for example *Rhodnius prolixus* and Triatoma spp.;

Bloodsucking adult flies: (e.g., horn fly [*Haematobia irritans*], horse fly [Tabanus spp.], stable fly [*Stomoxys calcitrans*], black fly [Simulium spp.], deer fly [Chrysops spp.], louse fly [*Melophagus ovinus*], tsetse fly [Glossina spp.], mosquitoes [Culex spp., Anopheles spp., and Aedes spp.]); and Parasitic fly maggots: (e.g., bot fly [*Oestrus ovis* and Cuterebra spp.], blow fly [Phaenicia spp.], screwworm [*Cochliomyia hominivorax*], cattle grub [Hypoderma spp.], fleeceworm).

The present invention also relates to a use of a compound of formula (I) or a salt thereof or a compound of formula (XX) or a salt thereof hereinbefore described as a therapeutic agent, preferably for animals, more preferably for domestic animals.

The veterinary composition may be sterile or non-sterile. It may be a liquid (e.g., aqueous) or solid (e.g., dry) composition, in particular a freeze-dried composition, from which, by addition of water or another liquid, orally effective solutions may be prepared.

The present invention also relates to a use of a compound of formula (I) or a salt thereof or a compound of formula (XX) or a salt thereof as hereinbefore defined for the manufacture of a veterinary composition for the control of parasites in or on an animal.

The present invention also relates to a method of cleaning animals in good health comprising the application to the animal of a compound of formula (I) or a salt thereof or a compound of formula (XX) or a salt thereof as hereinbefore defined to the animal.

The method of cleaning an animal is not a method of treatment by therapy of the animal body per se, because (a) the animal is in good health and requires no substantial treatment to correct a deficiency of health;

(b) the cleaning of the animal is not intended to be done by veterinary personnel, but by persons interested in the cleaning of the animal; and (c) the purpose of such cleaning is to avoid unpleasant conditions for humans and the environment which humans inhabit so as to not infest the said humans with arthropods carried by the animal.

By "carrier" is meant an organic or inorganic material, which can be natural or synthetic, and which is associated with the compound and which facilitates its application to the animal. This carrier is thus generally inert and should be arthropocidally acceptable. The carrier can be solid (e.g., clay, silicates, silica, resins, wax) or liquid (e.g., water, alcohols, ketones, oil solvents, polar aprotic solvents). An example of an oil solvent is corn oil. An example of a polar aprotic solvent is dimethyl sulfoxide.

The compounds of formula (II) wherein $R_{21}$, $R_{22}$, $R_{24}$, $R_{31}$, $R_{33}$ and X are as defined above may be prepared from the compounds of formula (III):

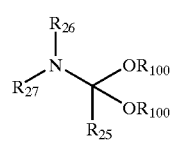

(III)

wherein $R_{21}$, $R_{22}$, $R_{31}$, $R_{33}$ and X are as defined above, using processes described in European Patent Publications 0511845 or 0659745, incorporated by reference herein and relied upon.

According to a feature of the present invention, compounds of formula (II) wherein $R_{21}$, $R_{22}$, $R_{31}$, $R_{33}$ and X are as defined above and $R_{24}$ is —N=C($R_{25}$)—$NR_{26}R_{27}$ wherein $R_{25}$, $R_{26}$ and $R_{27}$ are as defined above may be prepared by reacting a compound of formula (III) with a compound of formula (IV):

(IV)

$$\underset{R_{25}}{\overset{R_{26}}{\underset{|}{\overset{|}{N}}}}\underset{}{\overset{}{\underset{}{C}}}\underset{OR_{100}}{\overset{OR_{100}}{}}$$

wherein $R_{25}$, $R_{26}$ and $R_{27}$ are as defined above and $R_{100}$ is generally an alkyl group. The reaction is optionally conducted in the presence of a catalyst such as a mineral or organic acid (for example hydrochloric acid), generally using from 1 to 100 equivalents of (IV), preferably using 1 to 10 equivalents of (IV), and is preferably conducted in an organic solvent such as tetrahydrofuran, toluene, or N,N-dimethylformamide, at a temperature of from 0° C. to 150° C. Additional adjuvants such as drying agents (e.g., magnesium sulfate, potassium carbonate, or molecular sieves) may also be advantageous to the reaction. Compounds of formula (IV) are known or may be prepared by known procedures.

According to a feature of the present invention, compounds of formula (II) wherein $R_{21}$, $R_{22}$, $R_{31}$, $R_{33}$ and X are as defined above and $R_{24}$ is —N=C($R_{25}$)—$NR_{26}R_{27}$ wherein $R_{25}$, $R_{26}$ and $R_{27}$ are as defined above, may be prepared by the reaction of a compound of formula (V):

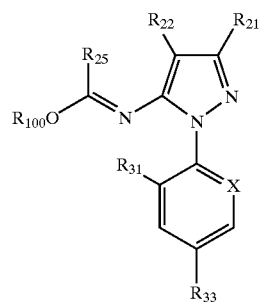

(V)

wherein $R_{21}$, $R_{22}$, $R_{25}$, $R_{31}$, $R_{33}$, X and $R_{100}$ are as defined above, with a compound of formula (VI):

wherein $R_{26}$ and $R_{27}$ are as defined above. The reaction is generally conducted using the same conditions as used for the preparation of compounds of formula (II) by the reaction of compounds of formula (III) with compounds of formula (IV).

According to a feature of the present invention, compounds of formula (II) wherein $R_{24}$ is —N=C($R_{25}$)—N$R_{27}R_{28}$, and $R_{21}$, $R_{22}$, $R_{25}$, $R_{27}$, $R_{31}$, $R_{33}$ and X are as defined above, and $R_{28}$ is COR$_{34}$ wherein $R_{34}$ is as defined above, may be prepared by the reaction of the corresponding compounds of formula (II) wherein $R_{24}$ is —N=C($R_{25}$)—NR$_{27}$H with an acid chloride of formula (VII):

$$R_{34}COCl \quad\quad (VII)$$

wherein $R_{34}$ is as defined above. The reaction is generally performed in the presence of a base such as a trialkylamine, for example triethylamine, in a solvent such as dichloromethane, at a temperature of from 0° C. to 50° C.

According to a feature of the present invention, compounds of formula (II) wherein $R_{24}$ is —N=C($R_{25}$)—NR$_{27}R_{28}$, and $R_{21}$, $R_{22}$, $R_{25}$, $R_{27}$, $R_{31}$, $R_{33}$ and X are as defined above and $R_{28}$ is —S(O)$_r R_{30}$ may be prepared by the reaction of the corresponding compound of formula (II) wherein $R_{24}$ is —N=C($R_{25}$)—NR$_{27}$H with a sulfonyl chloride or a sulfenyl chloride of formula (VIII):

$$R_{30}S(O)_rCl \quad\quad (VIII)$$

The reaction is generally performed in the presence of a weak base such as a trialkylamine for example triethylamine, or pyridine in a solvent such as dichloromethane, at a temperature of from 0° C. to 50° C.

Compounds of formulae (VI), (VII) and (VIII) are known or may be prepared by known procedures.

Compounds of formulae (III) and (V) may be generally prepared according to known processes, for example as described in International Patent Publications WO 87/03781, WO 93/06089, and WO 94/21606, WO 97/07102, WO 98/24767, WO 98/28277, WO 98/28278 and WO 98/28279, European Patent Publications 0295117, 0846686, and U.S. Pat. No. 5,232,940.

In another aspect of the present invention, compounds of formula (XX) wherein $R_{204}$ is —N($R_{205}$)C(O)CR$_{206}R_{207}R_{208}$, N($R_{205}$)C(O)aryl, or N($R_{205}$)C(O)OR$_{207}$ are generally prepared from compounds of formula (XXI):

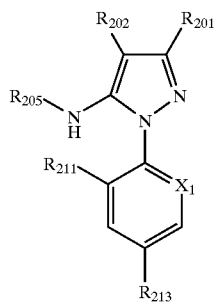

by reaction with halides of formulae X$_2$C(O)CR$_{206}R_{207}R_{208}$, X$_2$C(O)aryl, or X$_2$C(O)OR$_{207}$, respectively, wherein $R_{201}$, $R_{202}$, $R_{205}$, $R_{206}$, $R_{207}$, $R_{208}$, $R_{211}$, $R_{213}$, and X$_1$ are defined above and wherein X$_2$ is a halogen atom. The reaction is generally carried out in the presence of a base, generally using from 1 to 10 molar equivalents of the halide, and is preferably conducted in the presence of an organic solvent such as tetrahydrofuran, methylene chloride, at a temperature of from 0° C. to 150° C.

Compounds of formula (XXI) may be prepared from a compound of formula (XXII):

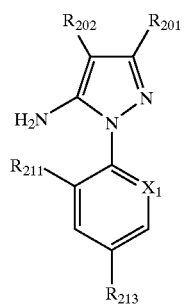

by reaction with a compound of formula (XXIII):

$$X_2R_{205} \quad\quad (XXIII)$$

wherein $R_{201}$, $R_{202}$, $R_{205}$, $R_{211}$, $R_{213}$, X$_1$ and X$_2$ are defined above. Compounds of formula (XXIII) are generally known in the art as alkylhalides or substituted alkythalides. Compounds of formula (XXII) may be prepared by methods described in International Patent Publications WO 87/03781, WO 93/06089, WO 94/21606, WO 97/07102, WO 98/24767, WO 98/28277, WO 98/28278 and WO 98/28279, European Patent Publications 0295117, 0659745, 0846686, and U.S. Pat. No. 5,232,940, or other methods known to the person skilled in the art.

Alternatively compounds of formula (XXI) may be prepared by reduction of compounds of formula (XXIV):

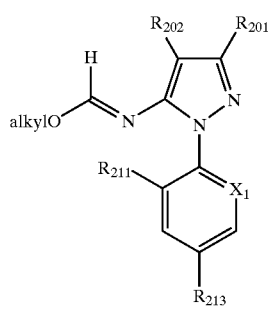

wherein $R_{201}$, $R_{202}$, $R_{211}$, $R_{213}$ and X$_1$ are defined above. The reduction generally is effected by the use of a standard hydride ion donor, for example sodium borohydride or sodium cyanoborohydride. The reaction is generally effected in an polar solvent such as ethanol or methanol and generally using from 1 to 10 molar equivalents of the hydride, and is preferably conducted at a temperature of from −100° C. to 150° C.

Compounds of formula (XXIV) may be prepared using methods described in EP 0295117, WO 97/22593 or other methods known to those skilled in the art.

In another aspect of the invention there are provided the compounds 3-cyano-1-(2,6-dichloro-4-trifluoromethylphenyl)-5-ethoxymethylideneamino-4-trifluoromethylsulfinylpyrazole and 3-cyano-1-(2,6-dichloro-4-trifluoromethylphenyl)-5-methylamino-4-trifluoromethylsulfinylpyrazole which are useful intermediates for the preparation of compounds for use according to the present invention.

BIOLOGICAL EXAMPLE 1

Compounds 1-1, 2-1, 3-1, 4-1, 11-1, 13-1, 28-1, 31-1, 32-1, 36-1, 37-1, 38-1, 1-3, 2-3, 3-3, 4-3, 6-3, 41-3, 1-5, 2-5, 3-5, 6-5, 11-5, 27-5, 28-5, 1-7, 3-7, 5-7, 1-9, 1-11, 6-11, 7-11, 1-12, 11-12, 13-12, 67-1, 68-1, 69-1, 70-1, 72-1 75-1, 76-1, 77-1, 78-1, 79-1, 80-1, 81-1, 82-1, 115-1, 116-1, 117-1, 118-1, 119-1, 120-1, 121-1, 122-1, 123-1, 124-1, 211-1, 219, 220, 221, 222, 223, 224, 225, 226, 227, 228, 229, 230, 231, 232, 233, (R)3-3, (S)3-3, (R)1-7, (S)1-7, (R,S)1-9, (R,R)1-9, (S,R)1-9, (S,S) 1-9, (S)1-11, (R)1-11, 126-1, 127-1 and 130-1 were each formulated as a 30 mg/mL formulation in a 1:1 volume/volume solution of dimethyl sulfoxide and corn oil. Using this formulation, mixed breed dogs and cats were treated at a rate of 10 mg of the compound per kg (mg/kg)of body weight of the dog and 20 mg/kg of the cat treated. The animals were fasted for at least 8 hours prior to treatment, fed half of the daily ration immediately prior to treatment, then allowed access to the remainder of the daily ration immediately following treatment.

All dogs were infested with cat fleas (*Ctenocephalides felis*) and with ticks (*Rhipicephalus sanguineus*) 1 day prior to administration of the compound. Cats were only infested with fleas. The initial flea and tick counts were performed 1 day after the administration of the compounds. At 7, 14, 21 and 28 days after treatment the dogs were re-infested with ticks and 8, 15, 22 and 29 days after treatment the dogs and cats were re-infested with fleas. At 1, 9, 16, 23 and 30 days after treatment the control of fleas and ticks in treated dogs and cats was determined versus a group of infested dogs and cats which received a placebo consisting of a 1:1 volume/volume solution of dimethyl sulfoxide and corn oil. To determine the efficacies of the compounds, the arthropods were combed from the animals and counted.

In the animals treated with the compounds above, there was substantially no emesis after 2, 8 and 24 hours. Generally long-term control of fleas and ticks was provided in dogs. In the cats treated, there was commercially acceptable control of fleas for at least one day post treatment.

The results of this example were superior to those obtained with compounds of the prior art, for example, fipronil.

BIOLOGICAL EXAMPLE 2

The compounds listed below were formulated and tested as described in Biological Example 1, again at the dosage level of active ingredient of 10 mg/kg in dogs and 20 mg/kg in cats. Results at 1 DPT (day post-treatment) are tabulated below, where the compound numbers are the same as those listed in Tables 1, 2, 4, 5, 6, 7, 8, 9, 10, 11, 12 and 13 hereinabove.

| Compound Number | % Control 1 DPT (Fleas/Ticks) | % Emesis |
|---|---|---|
| DOG TESTING RESULTS | | |
| 211-1 | 99/51 | 0 |
| 219 | 97/80 | 33 |
| 224 | 38/6 | 0 |
| 230 | 100/80 | 0 |
| 232 | 99/35 | 0 |
| 233 | 100/77 | 0 |
| 1-1 | 91/82 | 0 |
| 2-1 | 100/100 | 0 |
| 3-1 | 100/96 | 0 |
| 13-1 | 99/97 | 0 |
| 28-1 | 89/75 | 0 |
| 36-1 | 71/92 | 0 |
| 1-3 | 94/95 | 0 |
| 2-3 | 100/99 | 33 |
| 3-3 | 100/98 | 0 |
| 4-3 | 100/100 | 33 |
| 41-3 | 100/98 | 33 |
| 1-5 | 98/84 | 0 |
| 2-5 | 100/95 | 33 |
| 3-5 | 100/100 | 33 |
| 27-5 | 100/100 | 0 |
| 28-5 | 100/74 | 0 |
| 1-7 | 100/97 | 0 |
| 3-7 | 100/100 | 0 |
| 7-7 | 29/66 | 0 |
| 1-9 | 100/100 | 0 |
| 1-11 | 100/100 | 0 |
| 6-11 | 100/98 | 0 |
| 7-11 | 100/100 | 0 |
| 3-12 | 99/97 | 0 |
| 67-1 | 100/100 | 33 |
| 68-1 | 100/77 | 0 |
| 69-1 | 98/94 | 0 |
| 70-1 | 99/100 | 0 |
| 71-1 | 100/100 | 0 |
| 72-1 | 100/97 | 0 |
| 73-1 | 100/100 | 0 |
| 74-1 | 99/87 | 0 |
| 75-1 | 89/57 | 0 |
| 76-1 | 100/86 | 0 |
| 77-1 | 98/10 | 0 |
| 78-1 | 96/94 | 0 |
| 79-1 | 96/86 | 0 |
| 80-1 | 100/94 | 0 |
| 81-1 | 76/66 | 0 |
| 82-1 | 86/90 | 0 |
| 116-1 | 79/100 | 0 |
| 120-1 | 97/78 | 0 |
| 122-1 | 100/95 | 0 |
| 123-1 | 74/0 | 0 |
| 126-1 | 31/45 | 0 |
| 127-1 | 100/97 | 0 |
| 130-1 | 100/100 | 0 |

| Compound Number | % Control 1 DPT (Fleas) | %Emesis |
|---|---|---|
| CAT TESTING RESULTS | | |
| 219 | 100 | 25 |
| 230 | 98 | 0 |
| 232 | 100 | 0 |
| 233 | 95 | 0 |
| 1-1 | 99 | 0 |
| 2-1 | 100 | 0 |
| 3-1 | 100 | 0 |
| 13-1 | 61 | 0 |
| 28-1 | 100 | 0 |
| 36-1 | 100 | 25 |
| 37-1 | 76 | 0 |
| 38-1 | 87 | 0 |
| 1-3 | 87 | 0 |
| 2-3 | 100 | 0 |
| 3-3 | 100 | 0 |

-continued

| | | |
|---|---|---|
| 4-3 | 100 | 25 |
| 1-5 | 0 | 33 |
| 2-5 | 100 | 0 |
| 3-5 | 100 | 0 |
| 27-5 | 100 | 0 |
| 1-7 | 100 | 25 |
| 3-7 | 100 | 0 |
| 8-7 | 100 | 0 |
| (S)1-7 | 99 | 0 |
| (R)1-7 | 100 | 0 |
| 1-9 | 100 | 0 |
| 1-11 | 98 | 0 |
| 6-11 | 98 | 0 |
| 7-11 | 100 | 0 |
| 1-12 | 79 | 0 |
| 3-12 | 97 | 25 |
| 67-1 | 53 | 0 |
| 68-1 | 100 | 0 |
| 69-1 | 100 | 0 |
| 70-1 | 85 | 0 |
| 71-1 | 100 | 50 |
| 72-1 | 99 | 0 |
| 73-1 | 93 | 0 |
| 74-1 | 100 | 0 |
| 75-1 | 71 | 25 |
| 76-1 | 100 | 0 |
| 77-1 | 99 | 0 |
| 79-1 | 87 | 0 |
| 80-1 | 99 | 0 |
| 81-1 | 100 | 0 |
| 82-1 | 93 | 0 |
| 116-1 | 100 | 0 |
| 117-1 | 45 | 0 |
| 119-1 | 99 | 0 |
| 120-1 | 100 | 0 |
| 121-1 | 100 | 0 |
| 123-1 | 100 | 25 |
| 124-1 | 92 | 0 |
| 126-1 | 99 | 0 |
| 127-1 | 84 | 0 |
| 130-1 | 93 | 25 |

BIOLOGICAL EXAMPLE 3

A representative compound of formula (XX) of the invention was compared with a representative compound of Huang et al U.S. Pat. No. 5,556,873. The compounds tested were the following:

Compound of the Invention: 1-(2,6-dichloro-4-trifluoromethylphenyl)-3-cyano-4-trifluoromethylthio-5-(N-methyl)$_m$ethoxyacetamidopyrazole Huang et al Compound #1: 1-(2,6-dichloro-4-trifluoromethylphenyl)-3-cyano-4-trifluoromethylthio-5-(methoxyacetamido)pyrazole Testing was carried out as described in Biological Example 1. The compound of the invention, tested in a group of 3 dogs at 10 mg/kg, gave 93% control of fleas even at 30 DPT and 100% control of ticks at 30 DPT, with no emesis (0/3); tested in a group of 4 cats at 20 mg/kg, the compound of the invention gave 100% control of fleas for at least a one month period with no vomiting. In contrast, the Huang et al compound, tested in a group of 3 dogs at 10 mg/kg, gave <50% control of fleas after only 9 DPT and <50% control of ticks after 9 DPT, with no emesis (0/3). The Huang et al compound was deemed to have insufficient activity to be tested in cats.

The following non-limiting Synthesis Examples illustrate the preparation of compounds of formula (I) and the Reference Examples illustrate the preparation of intermediates used in their synthesis.

SYNTHESIS EXAMPLE 1

A solution of 5-amino-3-cyano-1-(2,6-dichloro-4-trifluoromethylphenyl)-4-trifluoromethylthiopyrazole (1 g) in N,N-dimethylformamide dimethyl acetal was heated at 50° C. for 1 hour. Evaporation of solvents gave 3-cyano-1-(2,6-dichloro-4-trifluoromethylphenyl)-5-N'-dimethylaminomethylideneamino-4-trifluoromethylthiopyrazole m.p. 141° C.

By proceeding in a similar manner the following compounds were also prepared:

3-cyano-1-(2,6-dichloro-4-trifluoromethylphenyl)-5-N'-dimethylaminomethylideneamino-4-trifluoromethylsulfonylpyrazole m.p. 209° C.; and 3-cyano-1-(2,6-dichloro-4-trifluoromethylphenyl)-5-N'-dimethylaminomethylideneamino-4-trifluoromethylsulfinylpyrazole m.p. 207° C.

SYNTHESIS EXAMPLE 2

A solution of 3-cyano-1-(2,6-dichloro-4-trifluoromethylphenyl)-5-ethoxymethylideneamino-4-trifluoromethylthiopyrazole (5 g) in ethanol was treated with benzylamine (11.4 ml), stirred overnight, evaporated and purified by reverse-phase column chromatography (C-18 stationary phase column, eluting with MeOH/water) to give 5-N'-benzylaminomethylideneamino-3-cyano-1-(2,6-dichloro-4-methylphenyl)-4-trifluoromethylthiopyrazole (1.18 g), m.p. 113° C.

By proceeding in a similar manner the compounds of formula (II) wherein $R_{21}$ is CN; $R_{24}$ is —N=CH—NHR$_{26}$; $R_{31}$ is Cl; X is C—Cl; and $R_{33}$ is $CF_3$ shown in the Table below were also prepared.

TABLE

| Compound No. | $R_{22}$ | $R_{26}$ | M.P. ° C. |
|---|---|---|---|
| 21 | $SCF_3$ | $CH_2CN$ | 175 |
| 211-1 | $SCF_3$ | $CH_2CF_3$ | 130 |
| 222 | $SCF_3$ | $CH_3$ | 173 |
| 223 | $SOCF_3$ | $CH_{2Ph}$ | 173 |
| 225 | $SOCF_3$ | $CH_3$ | 144 |
| 226 | $SOCF_3$ | $CH_3$ | 144 |
| 227 | $SOCF_3$ | $CH_2CF_3$ | 175 |
| 228 | $SO_2CF_3$ | 2-propynyl | 149 |
| 229 | $SO_2CF_3$ | $CH_2Ph$ | 182 |
| 230 | $SO_2CF_3$ | $CH_2CF_3$ | 183 |
| 209-1 | $SCF_3$ | iPr | |
| 207-1 | $SCF_3$ | $CH_2CH_3$ | 141 |

REFERENCE EXAMPLE 1

A solution of 5-amino-3-cyano-1-(2,6-dichloro-4-trifluoromethylphenyl)-4-trifluoromethylthiopyrazole (500 g) in triethyl orthoformate was treated with concentrated hydrochloric acid (10 ml) and heated at 50° C. After 8 hours the reaction mixture was evaporated to give a solid which was washed (heptane) and air-dried to give 3-cyano-1-(2,6-dichloro-4-trifluoromethylphenyl)-5-ethoxymethylideneamino-4-trifluoromethylthiopyrazole (217 g), m.p. 68° C.

By proceeding in a similar manner the following intermediates were also prepared:

3-cyano-1-(2,6-dichloro-4-trifluoromethylphenyl)-5-ethoxymethylideneamino-4-trifluoromethylsulfinylpyrazole, m.p. 63° C.; and 3-cyano-1-(2,6-dichloro-4-trifluoromethylphenyl)-5-ethoxymethylideneamino-4-trifluoromethylsulfonylpyrazole, m.p.118° C.

SYNTHESIS EXAMPLE 3

3-Cyano-1-(2,6-dichloro-4-trifluoromethylphenyl)-5-methylamino-4-trifluoromethylsulfinylpyrazole (111.55 g, 0.247 mole), triethylamine (62.45 g, 0.618 mole), 4-dimethylaminopyridine (3 g, 0.0247 mole), and tetrahydrofuran (700 ml) was combined. The resulting solution was heated to 45° C. and ethoxyacetyl chloride (45.2 g, 0.37 mmol) was added dropwise over 10 min. After 1 h, the mixture was evaporated to a brown residue, which was dissolved in 500 ml of ethyl acetate and washed with 2×300 ml of water. The organic phase was dried over magnesium sulfate, filtered, and evaporated to a brown oil. The oil was triturated with 1 L of hot cyclohexane. The resulting solids were collected by filtration and washed with 500 ml of hot cyclohexane, then air dried to afford compound 3-3 as a beige powder (116.7 g). Evaporation of the mother liquors afforded a second crop of compound 3-3 (8.4 g).

In a similar fashion or by modifications according to methods known to the skilled addressee, the following compounds were prepared. The compound numbers in the left column refer to the Tables cited above.

| Compound Number | Mass Spectral molecular ion + 1 (M + 1) |
|---|---|
| 1-1 | 477 |
| 2-1 | 507 |
| 3-1 | 521 |
| 4-1 | 535 |
| 11-1 | 505 |
| 13-1 | 549 |
| 28-1 | 537 |
| 31-1 | 517 |
| 32-1 | 531 |
| 36-1 | 535 |
| 37-1 | 521 |
| 38-1 | 535 |
| 1-3 | 593 |
| 2-3 | 523 |
| 3-3 | 537 |
| 4-3 | 551 |
| 6-3 | 491 |
| 41-3 | 473 |
| 1-5 | 509 |
| 2-5 | 539 |
| 3-5 | 553 |
| 6-5 | 523 |
| 11-5 | 537 |
| 27-5 | 579 |
| 28-5 | 593 |
| 1-7 | 533 |
| 3-7 | 561 |
| 5-7 | 575 |
| 1-9 | 549 |
| 1-11 | 565 |
| 6-11 | 591 |
| 7-11 | 605 |
| 1-12 | 535 |
| 11-12 | 565 |
| 13-12 | 579 |
| 67-1 | 493 |
| 68-1 | 507 |
| 69-1 | 521 |
| 70-1 | 521 |
| 72-1 | 521 |
| 75-1 | 521 |
| 76-1 | 535 |
| 77-1 | 549 |
| 78-1 | 549 |
| 79-1 | 521 |
| 80-1 | 535 |
| 81-1 | 549 |
| 82-1 | 549 |
| 115-1 | 505 |
| 116-1 | 535 |
| 117-1 | 503 |
| 118-1 | 521 |
| 119-1 | 549 |
| 120-1 | 583 |
| 121-1 | 547 |
| 122-1 | 551 |
| 123-1 | 491 |
| 124-1 | 505 |
| 126-1 | 507 |
| 127-1 | 607 |
| 130-1 | 529 |

REFERENCE EXAMPLE 2

Step A: Preparation of 3-Cyano-1-(2,6-dichloro-4-trifluoromethylphenyl)-5-ethoxymethylideneamino-4-trifluoromethylsulfinylpyrazole.

A 12-L three-necked flask fitted with an overhead stirrer, heating mantle, water separator (e.g. Dean Stark trap) with condenser was placed under a nitrogen atmosphere and charged with 1.475 kg (3.37 moles) of fipronil and 6 L of triethyl orthoformate. The suspension was heated to reflux over 2.5 h, then at reflux for 3 h with collection and removal of the distillate. The mixture was cooled to room temperature, then evaporated under reduced pressure at a bath temperature of 60–80° C., then at 50° C. overnight. The resulting beige solid, 1.717 kg (95.8% by HPLC, 3.335 moles, 99% purity corrected yield) was used without further purification (m.p. about 63° C.).

Step B: Preparation of 3-Cyano-1-(2,6-dichloro-4-trifluoromethylphenyl)-5-methylamino-4-trifluoromethylsulfinylpyrazole.

A 50 L reactor was charged with 3-cyano-1-(2,6-dichloro-4-trifluoromethylphenyl)-5-ethoxymethylideneamino-4-trifluoromethylsulfinylpyrazole (1.645 g, 3.335 moles) and absolute ethanol (16 L) under nitrogen. The solution was cooled to 10° C., and sodium borohydride (266 g, 7.03 moles) was added slowly such that the temperature remained generally below 35° C. After 6.75 h, some additional sodium borohydride (25 g, 0.66 mole) was added and stirring was continued overnight. Acetic acid (1.3 L, 22.7 moles) was added to quench, followed by 16 L of water. The resulting precipitate was collected by filtration, washed with water, and air-dried. Recrystallization from methanol afforded 3-cyano-1-(2,6-dichloro-4-trifluoromethylphenyl)-5-methylamino-4-trifluoromethylsulfonylpyrazole (350 g) as an off-white solid (m.p. about 227° C.).

While the invention has been described in terms of various preferred embodiments, the person skilled in the art will appreciate that various modifications, substitutions, omissions and changes can be made without departing from the spirit thereof. Accordingly, it is intended that the scope of the present invention be limited solely by the scope of the following claims, including equivalents thereof.

What is claimed is:

1. A method of controlling parasites in or on an animal in need of such control, said method comprising orally administering to said animal a parasiticidally effective, substantially non-emetic amount of a compound having the formula (XX):

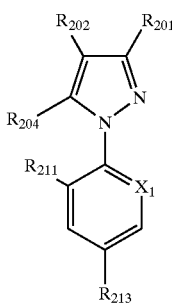

(XX)

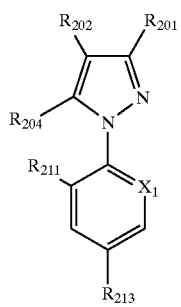

(XX)

wherein:

$R_{201}$ is cyano;

$R_{202}$ is $S(O)_hR_{203}$;

$R_{203}$ is alkyl or haloalkyl;

$R_{204}$ is —$N(R_{205})C(O)CR_{206}R_{207}R_{208}$;

$R_{205}$ is alkyl, haloalkyl, cycloalkyl, halocycloalkyl, cycloalkylalkyl or halocycloalkylalkyl;

$R_{206}$ is alkoxy, haloalkoxy, alkoxyalkyl or haloalkoxyalkyl;

$R_{207}$ and $R_{208}$ are each hydrogen;

$X_1$ is nitrogen or C—$R_{212}$;

$R_{211}$ and $R_{212}$ are, independently, halogen, hydrogen, CN or $NO_2$;

$R_{213}$ is halogen, haloalkyl, haloalkoxy, —$S(O)_kCF_3$, or —$SF_5$; and h and k are, independently, 0, 1 or 2;

or a veterinarily acceptable salt thereof.

2. A method according to claim 1, wherein, in the compound of formula (XX):

$R_{205}$ is alkyl, haloalkyl, cycloalkyl, cycloalkylalkyl or halocycloalkylalkyl; and $R_{206}$ is alkoxy or haloalkoxy.

3. The method according to claim 1, wherein the animal is a domestic animal.

4. The method according to claim 3, wherein the domestic animal is a cat or dog.

5. The method according to claim 1, wherein the compound of formula (XX) is orally administered to an animal in a dosage range of from 0.1 to 500 mg/kg.

6. The method according to claim 1, wherein the compound of formula (XX) is administered at a frequency of from about once per week to about once per year.

7. The method according to claim 5, wherein the compound of formula (XX) is administered at a frequency of from about once per week to about once per year.

8. A method of controlling parasites in or on an animal in need of such control, said method comprising orally administering to said animal a parasiticidally effective, substantially non-emetic amount of a compound having the formula (XX):

wherein:

$R_{201}$ is cyano;

$R_{202}$ is $S(O)_hCF_3$;

$R_{204}$ is $N(R_{205})C(O)CR_{206}R_{207}R_{208}$;

$R_{205}$ is alkyl or cycloalkylalkyl;

$R_{206}$ is alkoxy, alkoxyalkyl or haloalkoxy;

$R_{207}$ is hydrogen;

$R_{208}$ is hydrogen;

$R_{211}$ is Cl;

$X_1$ is C—Cl;

$R_{213}$ is $CF_3$ or $SF_5$; and h is 0, 1 or 2;

or a veterinarily acceptable salt thereof.

9. A method according to claim 3, wherein, in the compound of formula (XX), $R_{202}$ is $SCF_3$.

10. A method according to claim 9, wherein, in the compound of formula (XX), $R_{205}$ is methyl, ethyl, n-propyl, isopropyl, n-butyl or cyclopropylmethyl, and $R_{206}$ is methoxy, ethoxy, isopropoxy, n-butyloxy, methoxymethyl, ethoxyethyl or $OCH_2CF_3$.

11. A method according to claim 10, wherein, in the compound of formula (XX), $R_{213}$ is $CF_3$.

12. The method according to claim 17, wherein, in the compound of formula (XX):

(a) $R_{205}$ is methyl and $R_{206}$ is methoxy;

(b) $R_{205}$ is methyl and $R_{206}$ is ethoxy;

(c) $R_{205}$ is methyl and $R_{206}$ is isopropoxy;

(d) $R_{205}$ is n-propyl and $R_{206}$ is ethoxy;

(e) $R_{205}$ is cyclopropylmethyl and $R_{206}$ is ethoxy;

(f) $R_{205}$ is methyl and $R_{206}$ is methoxymethyl; or (g) $R_{205}$ is methyl and $R_{206}$ is ethoxymethyl.

13. A method according to claim 8, wherein, in the compound of formula (XX), $R_{202}$ is $S(O)CF_3$.

14. A method according to claim 13, wherein, in the compound of formula (XX), $R_{205}$ is methyl, ethyl, n-propyl, isopropyl, n-butyl or cyclopropylmethyl, and $R_{206}$ is methoxy, ethoxy, isopropoxy, n-butyloxy, methoxymethyl, ethoxymethyl or $OCH_2CF_3$.

15. A method according to claim 14, wherein, in the compound of formula (XX), $R_{213}$ is $CF_3$.

16. The method according to claim 15, wherein, in the compound of formula (XX):

(a) $R_{205}$ is methyl and $R_{206}$ is methoxy;

(b) $R_{205}$ is methyl and $R_{206}$ is ethoxy;

(c) $R_{205}$ is methyl and $R_{206}$ is isopropoxy; or (d) $R_{205}$ is methyl and $R_{206}$ is $OCH_2CF_3$.

17. The method according to claim 15, wherein, in the compound of formula (XX), $R_{205}$ is methyl and $R_{206}$ is ethoxy, said compound being the R enantiomer.

18. The method according to claim 15, wherein, in the compound of formula (XX), $R_{205}$ is methyl and $R_{206}$ is ethoxy, said compound being the S enantiomer.

19. A method according to claim 8, wherein, in the compound of formula (XX), $R_{202}$ is $S(O)_2CF_3$.

20. A method according to claim 19, wherein, in the compound of formula (XX), $R_{205}$ is methyl, ethyl, n-propyl, isopropyl, n-butyl or cyclopropylmethyl; and $R_{206}$ is methoxy, ethoxy, isopropoxy, n-butyloxy, methoxymethyl, ethoxymethyl or $OCH_2CF_3$.

21. A method according to claim 20, wherein, in the compound of formula (XX), $R_{213}$ is $CF_3$.

22. The method according to claim 21, wherein, in the compound of formula (XX):

(a) $R_{205}$ is methyl and $R_{206}$ is methoxy;

(b) $R_{205}$ is methyl and $R_{206}$ is ethoxy;

(c) $R_{205}$ is cyclopropylmethyl and $R_{206}$ is methoxy; or (d) $R_{205}$ is cyclopropylmethyl and $R_{206}$ is ethoxy.

23. A method according to claim 1, wherein, in the compound of formula (XX), $R_{202}$ is $SCF_3$, $S(O)CF_3$ or $S(O)_2CF_3$; $R_{211}$ is Cl; $X_1$ is C—Cl; $R_{213}$ is $CF_3$ or $SF_5$; $R_{205}$ is cyclopropyl; $R_{207}$ is hydrogen; $R_{208}$ is hydrogen; and $R_{206}$ is alkoxy.

24. A method according to claim 23, wherein, in the compound of formula (XX), $R_{206}$ is methoxy, ethoxy, isopropoxy or n-butyloxy.

25. A method according to claim 24, wherein, in the compound of formula (XX), $R_{213}$ is $CF_3$.

26. The method according to claim 25, wherein, in the compound of formula (XX):

(a) $R_{202}$ is $S(O)_2CF_3$ and $R_{206}$ is ethoxy; or (b) $R_{202}$ is $SCF_3$ and $R_{206}$ is ethoxy.

27. A method according to claim 8, wherein, in the compound of formula (XX), $R_{205}$ is alkyl; and $R_{206}$ is alkoxy.

28. A method according to claim 27, wherein, in the compound of formula (XX), $R_{205}$ is methyl; and $R_{206}$ is methoxy or ethoxy.

29. A method according to claim 28, wherein, in the compound of formula (XX), $R_{213}$ is $CF_3$.

30. The method according to claim 8, wherein the animal is a domestic animal.

31. The method according to claim 30, wherein the domestic animal is a cat or dog.

32. The method according to claim 8, wherein the compound of formula (XX) is orally administered to an animal in a dosage range of from 0.1 to 500 mg/kg.

33. The method according to claim 8, wherein the compound of formula (XX) is administered at a frequency of from about once per week to about once per year.

34. The method according to claim 32, wherein the compound of formula (XX) is administered at a frequency of from about once per week to about once per year.

35. A method of controlling parasites in or on an animal in need of such control, said method comprising orally administering to said animal a parasiticidally effective, substantially non-emetic amount of a compound having the formula (XX):

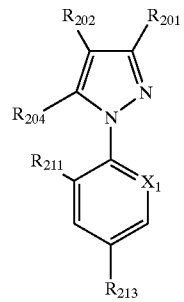

wherein:

$R_{201}$ is cyano;

$R_{202}$ is $S(O)_hCF_3$;

$R_{204}$ is —$N(R_{205})C(O)CR_{206}R_{207}R_{208}$;

$R_{205}$ is alkyl;

$R_{206}$ is alkoxy;

$R_{207}$ is hydrogen;

$R_{208}$ is hydrogen;

$X_1$ is C—Cl;

$R_{211}$ is Cl;

$R_{213}$ is —$CF_3$, or —$SF_5$; and h is 0, 1 or 2;

or a veterinarily acceptable salt thereof.

36. A method according to claim 35, wherein, in the compound of formula (XX), $R_{205}$ is methyl or ethyl.

37. A method according to claim 35, wherein, in the compound of formula (XX), $R_{206}$ is methoxy, ethoxy, propoxy or isopropoxy.

38. A method according to claim 36, wherein, in the compound of formula (XX), $R_{206}$ is methoxy, ethoxy, propoxy or isopropoxy.

39. A method according to claim 37, wherein, in the compound of formula (XX), $R_{206}$ is methoxy or ethoxy.

40. A method according to claim 38, wherein, in the compound of formula (XX), $R_{206}$ is methoxy or ethoxy.

41. A method according to claim 39, wherein, in the compound of formula (XX), $R_{205}$ is methyl.

42. A method according to claim 40, wherein, in the compound of formula (XX), $R_{205}$ is methyl.

43. A method according to claim 35, wherein, in the compound of formula (XX), $R_{202}$ is —$SOCF_3$, $R_{205}$ is methyl, $R_{206}$ is ethoxy and $R_{213}$ is $CF_3$.

44. The method according to claim 35, wherein the animal is a domestic animal.

45. The method according to claim 44, wherein the domestic animal is a cat or dog.

46. The method according to claim 35, wherein the compound of formula (XX) is orally administered to an animal in a dosage range of from 0 1 to 500 mg/kg.

47. The method according to claim 35, wherein the compound of formula (XX) is administered at a frequency of from about once per week to about once per year.

48. The method according to claim 46, wherein the compound of formula (XX) is administered at a frequency of from about once per week to about once per year.

49. A method of controlling parasites in or on an animal in need of such control, said method comprising orally administering to said animal a parasiticidally effective, substantially non-emetic amount of a composition comprising a parasiticidally effective, substantially non-emetic amount of a compound having the formula (XX):

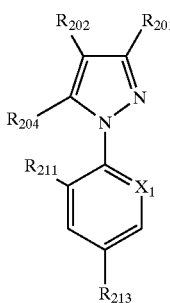

(XX)

wherein:

$R_{201}$ is cyano;

$R_{202}$ is $S(O)_h R_{203}$;

$R_{203}$ is alkyl or haloalkyl;

$R_{204}$ is $-N(R_{205})C(O)CR_{206}R_{207}R_{208}$;

$R_{205}$ is alkyl, haloalkyl, cycloalcyl, halocycloalkyl, cycloalkylalkyl or halocycloalkylalkyl;

$R_{206}$ is alkoxy, haloalkoxy, alkoxyalkyl or haloalkoxyalkyl;

$R_{207}$ and $R_{208}$ are each hydrogen;

$X_1$ is nitrogen or $C-R_{212}$;

$R_{211}$ and $R_{212}$ are, independently, halogen, hydrogen, CN or $NO_2$;

$R_{213}$ is halogen, haloalkyl, haloalkoxy, $-S(O)_k CF_3$, or $-SF_5$; and h and k are, independently, 0, 1, or 2;

or a veterinarily acceptable salt thereof;

and a veterinarily acceptable carrier therefor.

50. A method according to claim 49, wherein said composition is a veterinary composition comprising, in oral unit dosage form:

(a) a parasiticidally effective, substantially non-emetic amount of a compound having the formula (XX) as defined in claim 49, or a veterinarily acceptable salt thereof; and (b) a veterinarily acceptable carrier therefor.

51. A method according to claim 50, wherein the oral unit dosage amount of the compound of formula (XX) in said composition is from 0.1 to 500 mg per kg of animal body weight.

52. A method of controlling parasites in or on an animal in need of such control, said method comprising orally administering to said animal a parasiticidally effective, substantially non-emetic amount of a composition comprising a parasiticidally effective, substantially non-emetic amount of a compound having the formula (XX):

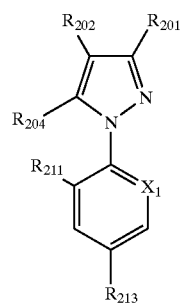

(XX)

wherein:

$R_{201}$ is cyano;

$R_{202}$ is $S(O)_h CF_3$;

$R_{204}$ is $-N(R_{205})C(O)CR_{206}R_{207}R_{208}$;

$R_{205}$ is alkyl;

$R_{206}$ is alkoxy;

$R_{207}$ is hydrogen;

$R_{208}$ is hydrogen;

$X_1$ is $C-Cl$;

$R_{211}$ is Cl;

$R_{213}$ is $-CF_3$, or $-SF_5$; and h is 0, 1 or 2;

or a veterinarily acceptable salt thereof;

and a veterinarily acceptable carrier therefor.

53. A method according to claim 52, wherein said composition is a veterinary composition comprising, in oral unit dosage form:

(a) a parasiticidally effective, substantially non-emetic amount of a compound having the formula (XX) as defined in claim 52, or a veterinarily acceptable salt thereof; and (b) a veterinarily acceptable carrier therefor.

54. A method according to claim 53, wherein the oral unit dosage amount of the compound of formula (XX) in said composition is from 0.1 to 500 mg per kg of animal body weight.

55. A method of controlling parasites in or on an animal in need of such control, said method comprising orally administering to said animal a parasiticidally effective, substantially non-emetic amount of a composition comprising a parasiticidally effective, substantially non-emetic amount of a compound having the formula (XX):

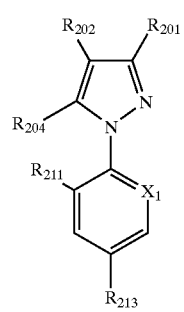

(XX)

wherein:

$R_{201}$ is cyano;

$R_{202}$ is $S(O)_h CF_3$;

$R_{204}$ is —N($R_{205}$)C(O)C$R_{206}R_{207}R_{208}$;

$R_{205}$ is alkyl or cycloalkylalkyl;

$R_{206}$ is alkoxy, alkoxyalkyl or haloalkoxy;

$R_{207}$ is hydrogen;

$R_{208}$ is hydrogen;

$R_{211}$ is Cl;

$X_1$ is Cl;

$R_{213}$ is $CF_3$ or $SF_5$; and h is 0, 1 or 2;

or a veterinarily acceptable salt thereof;
and a veterinarily acceptable carrier therefor.

56. A method according to claim 55, wherein said composition is a veterinary composition comprising, in oral unit dosage form:
(a) a parasiticidally effective, substantially non-emetic amount of a compound having the formula (XX) as defined in claim 55, or a veterinarily acceptable salt thereof; and
(b) a veterinarily acceptable carrier therefor.

57. A veterinary composition according to claim 56, wherein the oral unit dosage amount of the compound of formula (XX) in said composition is from 0.1 to 500 mg per kg of animal body weight.

* * * * *

UNITED STATES PATENT AND TRADEMARK OFFICE
CERTIFICATE OF CORRECTION

PATENT NO. : 6,630,499 B1  
DATED : October 7, 2003  
INVENTOR(S) : Scott Kevin Huber et al.

Page 1 of 1

It is certified that error appears in the above-identified patent and that said Letters Patent is hereby corrected as shown below:

Column 3,
Formula XX, change

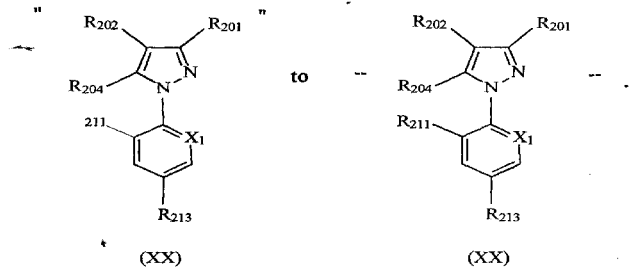

Column 7,
Formula II, change

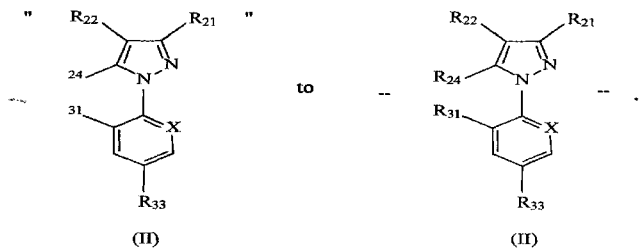

Column 30,
Line 39, change "claim 17" to -- claim 11 --.

Signed and Sealed this

Seventeenth Day of August, 2004

JON W. DUDAS  
*Acting Director of the United States Patent and Trademark Office*